United States Patent
Goldberg et al.

(10) Patent No.: US 12,343,246 B2
(45) Date of Patent: *Jul. 1, 2025

(54) ANCHOR DELIVERY SYSTEM AND METHOD

(71) Applicant: ESCALA MEDICAL LTD., Misgav (IL)

(72) Inventors: Edit Goldberg, Zichron Yaaqov (IL); Hagay Weisbrod, Jordan Valley (IL); Moran Sobol, Haifa (IL); Shahar Harari, Tel Aviv (IL)

(73) Assignee: ESCALA MEDICAL LTD., Misgav (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/142,681

(22) Filed: May 3, 2023

(65) Prior Publication Data

US 2023/0355368 A1    Nov. 9, 2023

Related U.S. Application Data

(63) Continuation of application No. 16/464,437, filed as application No. PCT/IL2017/051300 on Nov. 29, 2017, now Pat. No. 11,678,965.
(Continued)

(51) Int. Cl.
*A61F 2/00*   (2006.01)
*A61B 17/42*   (2006.01)
*A61B 17/00*   (2006.01)

(52) U.S. Cl.
CPC ............ *A61F 2/0022* (2013.01); *A61B 17/42* (2013.01); *A61B 2017/00407* (2013.01); *A61B 2017/00526* (2013.01); *A61B 2017/00862* (2013.01)

(58) Field of Classification Search
CPC ..... A61B 17/42; A61B 17/68; A61B 17/0487; A61B 17/12009; A61B 2017/0417;
(Continued)

(56) References Cited

U.S. PATENT DOCUMENTS

| | | | |
|---|---|---|---|
| 7,678,135 B2 * | 3/2010 | Maahs | A61B 17/0401 606/198 |
| 2005/0033363 A1 | 2/2005 | Bojarski | |

(Continued)

FOREIGN PATENT DOCUMENTS

EP    1598018 A1    11/2005

*Primary Examiner* — Tuan V Nguyen
(74) *Attorney, Agent, or Firm* — Momentum IP; Marc Van Dyke

(57) ABSTRACT

An apparatus for affixing a first tissue to a second tissue and methods of manufacturing and using the same. The apparatus comprises an elongated needle; a handle disposed at a proximal end of the elongated needle; a superelastic anchor disposed within the elongated needle, the anchor comprises: at least one normally-expanded elongated hook that is biased to a contracted state to fit within the elongated needle; a securing element; and an advancement mechanism triggerable by the handle and being configured to: eject the anchor out of a distal end of said elongated needle to allow the elongated hook to extend distally outward from the longitudinal axis of the elongated needle, into or beyond a tissue, and following the ejection of the anchor, eject the securing element from the apparatus to prevent movement of the anchor in at least one direction.

10 Claims, 19 Drawing Sheets

Related U.S. Application Data

(60) Provisional application No. 62/427,240, filed on Nov. 29, 2016.

(58) Field of Classification Search
CPC ...... A61B 2017/042; A61B 2017/0427; A61B 2017/0437; A61B 2017/00407; A61B 2017/00862; A61B 2017/00526; A61F 2/0004; A61F 2/0022; A61F 2002/0072
See application file for complete search history.

(56) References Cited

U.S. PATENT DOCUMENTS

| | | | |
|---|---|---|---|
| 2005/0261710 A1 | 11/2005 | Sakamoto | |
| 2009/0012561 A1 | 1/2009 | Johnstone | |
| 2010/0145362 A1* | 6/2010 | McLawhorn | ...... A61B 17/0401 |
| | | | 606/232 |
| 2015/0133997 A1* | 5/2015 | Deitch | ............... A61B 17/0401 |
| | | | 606/228 |

* cited by examiner

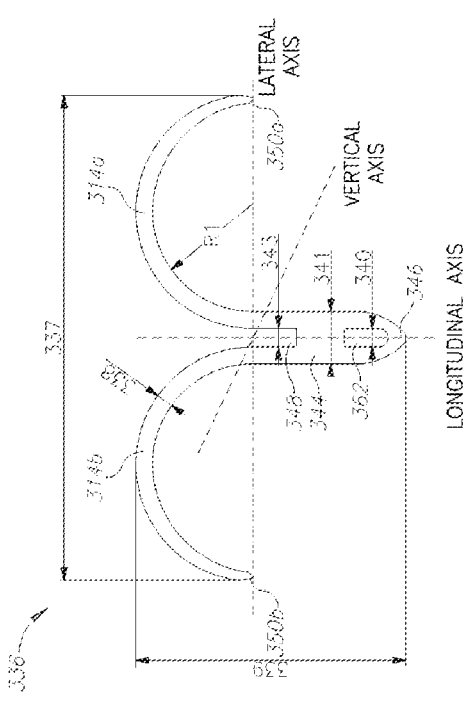
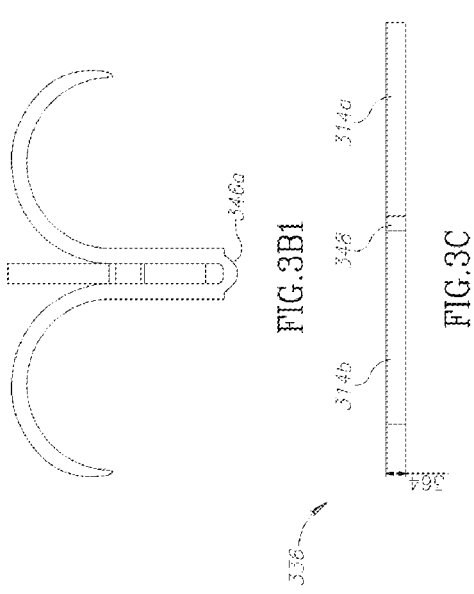
FIG.3B
FIG.3B1
FIG.3C

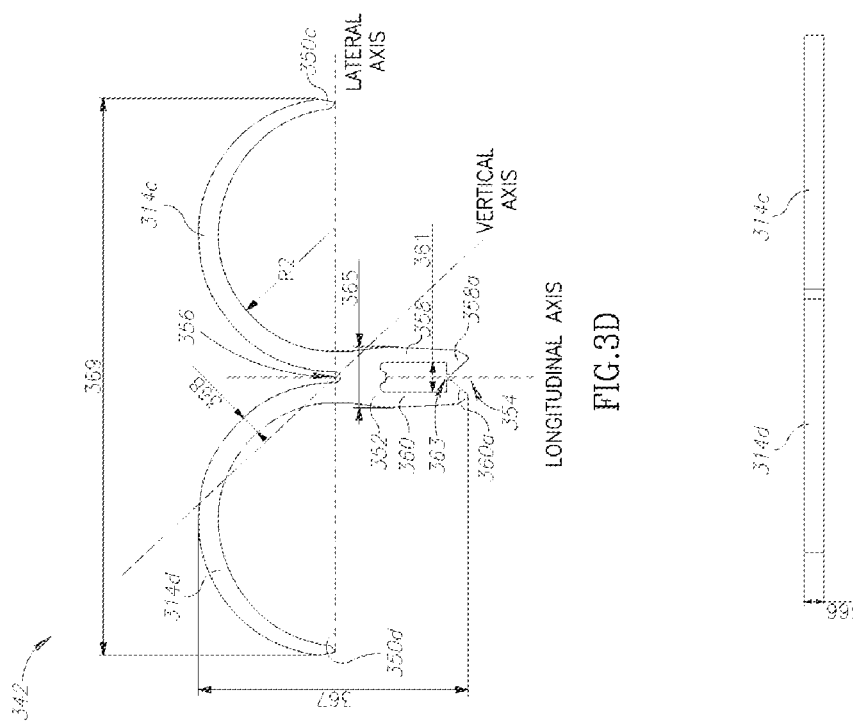

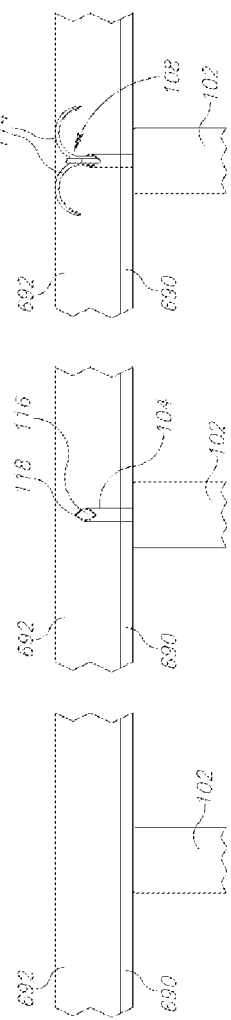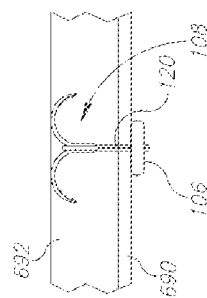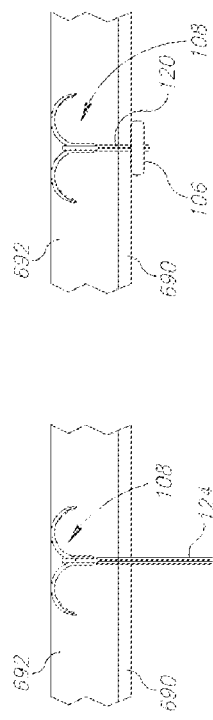

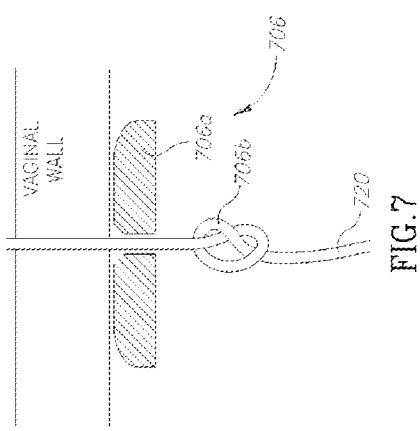
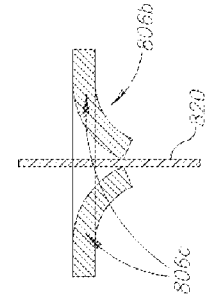
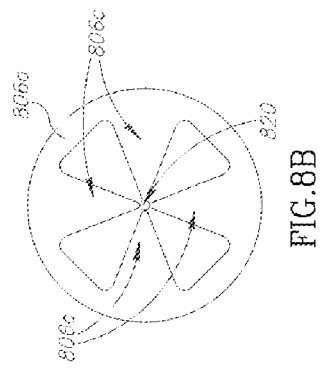
FIG.7
FIG.8A
FIG.8B

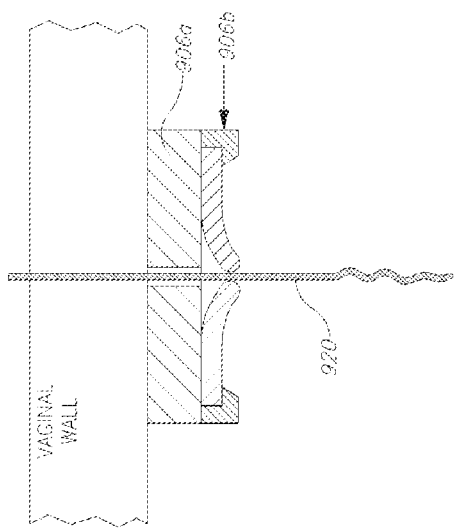
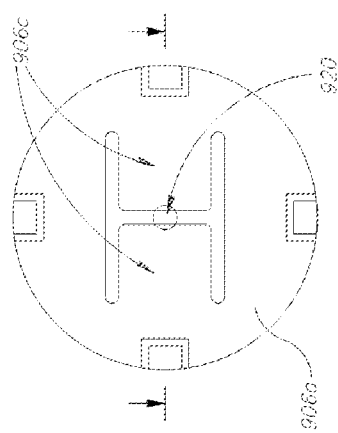
FIG. 9A
FIG. 9B

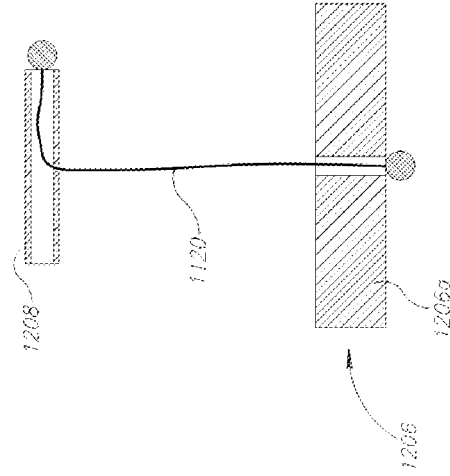
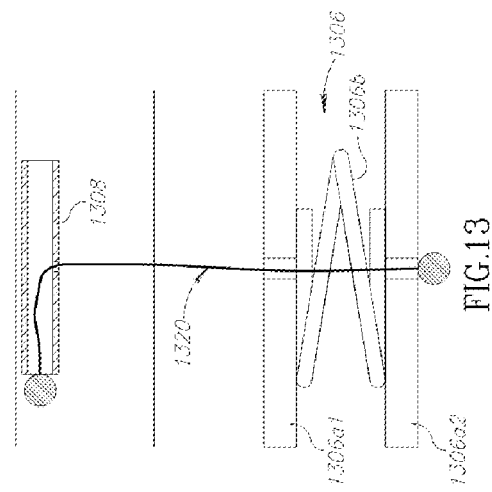
FIG.12
FIG.13

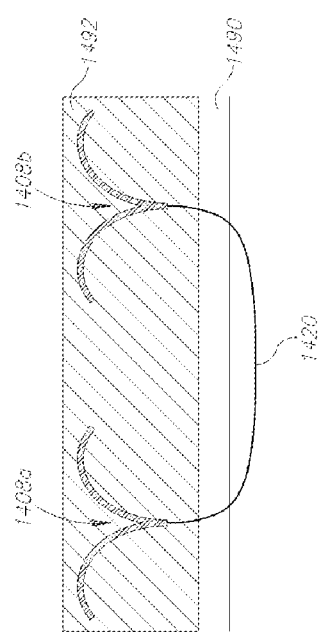

ANCHOR DELIVERY SYSTEM AND METHOD

CROSS-REFERENCE TO RELATED APPLICATIONS

PCT/IL2017/051300, filed on Nov. 29, 2017, is incorporated herein by reference in its entirety. PCT/IL2017/051300 claims priority to U.S. Provisional Patent Application No. 62/427,240, filed Nov. 29, 2016, entitled "Anchor Delivery System and Method", which is incorporated herein by reference in its entirety.

FIELD OF THE INVENTION

The invention relates to the field of tissue anchoring systems.

BACKGROUND

There are a variety of medical devices and procedures used for supporting internal portions of a patient's body such as for treating pelvic organ prolapse. The pelvic floor of a patient includes muscles and ligaments that support organs, such as the bladder, colon, urethra, uterus, cervix, small intestine, or rectum within a pelvic cavity. Pelvic organ prolapse occurs when this normal structural support stretches or weakens, causing the descent or drop of the organs. There are four main forms of pelvic organ prolapse. Cystocele is a weakening of the vaginal wall causing the bladder to protrude into the vagina. Rectocele is a weakening of the back wall of the vagina causing the rectum to protrude into the vagina. In vaginal vault prolapse (uterine prolapse) the uterus intrudes into the vagina from above, and in enterocele the small intestine descends and protrudes into the vagina.

One procedure for treating this type of disorder comprises securing the apex of the vagina to a sacrospinous ligament or other structurally supportive tissue within the pelvic region. In a majority of circumstances, anterior and posterior prolapses are caused by apical support defects. By supporting the vaginal apex region, most of the apically related prolapses of the vaginal area are relieved.

Conventional prolapse repair procedures require an incision through an abdominal or vaginal approach. In particular, these procedures include placing a mesh, graft, or other implant within the pelvic region of a patient. The mesh, graft, or other implant is delivered to the pelvic region through one or more incisions. Thus, this requires substantial surgery where a patient can be typically hospitalized for days after the surgery as part of their recovery.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in accordance with an embodiment, an apparatus comprising: an elongated needle; a handle disposed at a proximal end of said elongated needle; a superelastic anchor disposed within said elongated needle, said anchor comprising: at least one normally-expanded elongated hook that is biased to a contracted state to fit within said elongated needle; a securing element; a thread disposed inside said elongated needle and extending along at least a portion of the length of said elongated needle, wherein said thread is coupled to said anchor and is threaded through said securing element; and an advancement mechanism triggerable by said handle and being configured to: eject said anchor out of a distal end of said elongated needle to allow said elongated hook to extend distally outward from the longitudinal axis of the elongated needle, into or beyond a tissue, and following the ejection of said anchor, eject the securing element from the apparatus, to prevent movement of the anchor in at least one direction.

In some embodiments, the securing element is slidably disposed around the elongated needle.

In some embodiments, the securing element comprises an actuator configured to prevent sliding of the securing element over said thread in at least one direction. In some embodiments, the actuator of said securing element is a ratchet mechanism. In some embodiments, the actuator of said securing element is configured to exert force on said thread.

According to one aspect, there is provided an anchor comprising: a first planar anchoring element obtained from a sheet of a superelastic material, and comprising: a first proximal coupling portion having an aperture extending between a posterior side and an anterior side of said proximal coupling portion, and a distal pair of opposing hooks disposed co-planarly with said first proximal coupling portion and extending distally and laterally away in from said first proximal coupling portion; and a second planar anchoring element obtained from a sheet of a superelastic material, and comprising: a second proximal coupling portion comprising: a pair of spaced apart proximal arms each comprising a proximal protrusion, wherein said proximal protrusions of said arms protrude one towards the other, wherein a proximal distance between said proximal protrusions is less than a thickness measured from a posterior to an anterior side of said first coupling element, and a distal pair of opposing hooks disposed co-planarly with said second proximal coupling portion and extending distally and laterally away from said second proximal coupling portion, wherein said first and said second planar anchoring elements are structured to couple together upon insertion and latching of said proximal protrusions of said second planar anchoring element to said aperture of said first planar anchoring element.

According to one aspect, there is provided a method for manufacturing the anchor, said method comprising the steps of: obtaining the first planar anchoring element and said second planar anchoring element from at least one sheet of superelastic material; positioning said first and said second planar anchoring elements with their planes perpendicular to one another; and inserting and latching said proximal protrusions of said second planar anchoring element to said aperture of said first planar anchoring element.

In some embodiments, the obtaining is by employing a technique selected from the group consisting of: stamping, cutting, and forging.

According to one aspect, there is provided a method for ligament fixation, the method comprising the steps of: trans-vaginally introducing an elongated needle and sequentially piercing a vaginal wall and penetrating a ligament, such as the sacrospinous ligament, with a distal end of said elongated needle; ejecting a contracted anchor out of the distal end of said elongated needle such that elongated hook of said anchor extends distally outward from the longitudinal axis of the needle, into the ligament; and withdrawing said elongated needle to a position proximal to the vaginal wall, such as to expose a thread coupled to said anchor; and deploying a securing element against a proximal portion of the vaginal wall and actuating an actuator, to prevent the sliding of said securing element over said thread in at least one direction, thereby affixing the vaginal wall to the ligament.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIG. 3B is a schematic illustration showing a first planar anchoring element of the anchor of FIG. 3A, in accordance with an embodiment;

FIG. 3B(1) is a schematic illustration showing an alternative first planar anchoring element of the anchor of FIG. 3A, in accordance with an embodiment;

FIG. 3C is a distal end view of the first planar anchoring element of FIG. 3B, in accordance with an embodiment;

FIG. 3D is a schematic illustration showing a second planar anchoring element of the anchor of FIG. 3A, in accordance with an embodiment;

FIG. 3E is a distal end view of the second planar anchoring element of FIG. 3D, in accordance with an embodiment;

FIGS. 6A-6E are schematic illustrations, each illustrating a step of a method for affixing a vaginal wall to a ligament, in accordance with the apparatus of FIGS. 1A-E;

FIG. 7 is a side view of a securing element, in accordance with an embodiment;

FIGS. 8A-8B are a side view and a proximal end view, respectively, of a securing element in accordance with an embodiment;

FIGS. 9A-9B are a side view and a proximal end view, respectively, of a securing element in accordance with an embodiment;

FIG. 12 shows a thread coupled to an anchor a securing element, in accordance with an embodiment;

FIG. 13 shows a thread coupled to an anchor a securing element, in accordance with an embodiment; and FIG. 14 shows two anchors affixing a first tissue and a second tissue, in accordance with an embodiment.

DETAILED DESCRIPTION

Figure 1A:
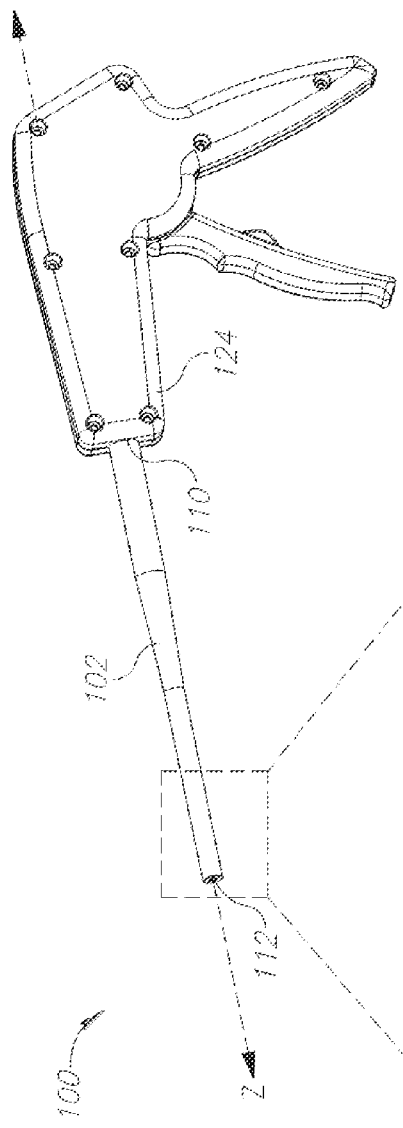
FIG. 1A shows a fully assembled view of an apparatus for affixing a first tissue to a second tissue, in accordance with an embodiment.

Disclosed herein is an apparatus for affixing a first tissue to a second tissue (e.g., a vaginal wall to a sacrospinous ligament), and a method for operating the apparatus. The fixation may either bring the two tissues in contact, or they may remain at a certain distance from each other, but prevented from being drawn apart beyond the distance permitted by the manner of fixation. In some embodiments, the first and the second tissue may refer to different portions of the same tissue. Further disclosed is a method of manufacturing the apparatus.

The apparatus may include an elongated needle for penetrating a tissue, which houses an anchor in a contracted configuration and a securing element. The securing element may be configured to prevent movement of the anchor in at least one direction relative to the securing element, following release of the anchor from the elongated needle. The securing element may interface with a tissue over a relatively large surface area, so as to spread the load it exerts on the tissue.

Optionally, the anchor or at least a portion thereof is biodegradable. Optionally, the anchor or at least a portion thereof is elastic. Optionally the anchor or at least a portion thereof is superelastic. Optionally, the anchor includes at least one normally-expanded distal hook that is biased to fit within the elongated needle and extends distally outward upon release from the elongated needle. Optionally, upon release of the anchor from the needle, the at least one hook extends distally outward from the longitudinal axis of the elongated needle into the tissue. Optionally, the anchor is released such that the at least one hook extends outside a distal surface of the tissue into a body lumen. In such embodiments, the anchor may be structured to include one or more T-bars rather than at least one hook.

Optionally, the apparatus includes a plurality of anchors. Optionally, the elongated needle may house the plurality of anchors. In such embodiments, the plurality of anchors may be deployed serially or sequentially. Alternatively, or additionally, the apparatus may include a plurality of elongated needles each housing at least one of the plurality of anchors so that plurality of anchors may be deployed simultaneously. The plurality of anchors may be coupled to one another. The plurality of anchors may be coupled to one another prior to deployment in a tissue. Alternatively, the plurality of anchors may be coupled to one another upon deployment in a tissue. Reference is now made to FIG. 14 which shows two anchors 1408a and 1408b affixing a second tissue 1492 to a first tissue 1490, in accordance with one embodiment. Two anchors 1408a and 1408b are deployed within second tissue 1492 (e.g., sacrospinous ligament). Optionally, anchors 1408a and 1408b are couple together by a band 1420 that is wide enough (at least where it contacts the proximal surface of a first tissue 1490) to prevent it from cutting through the first tissue. Band 1420 may spread between anchors 1408a and 1408b proximally to a first tissue 1490 (e.g., vaginal wall) to affix the first tissue (e.g., vaginal wall) to second tissue 1492. Optionally, a securing element (not shown) may be coupled to band 1420 and pushed against the proximal surface of first tissue 1490 to further prevent band 1420 from cutting through tissue.

Optionally, the securing element may engage with a proximal portion of the anchor thereby preventing movement of the anchor in at least one direction relative to the securing element. Optionally, the securing element may engage with the anchor via a connecting element such as, for a non-limiting example a thread. The thread is optionally a surgical thread (sometimes referred to as a surgical "suture"), which may be bioabsorbable or non-bioabsorbable. Suitable bioabsorbable materials include, for example, polyglycolic acid, polylactic acid, monocryl, and polydioxanone. Suitable non-bioabsorbable materials include, for example, nylon, polyester, PVDF (Polyvinylidene fluoride), and polypropylene. The thread may be a braided thread, a monofilament line, or a multifilament line. The thread may be made of metal or plastic, or of any biocompatible material. The thread may be rigid or tensile.

A person skilled in the art will appreciate that a thread (e.g., made of a permanent suture) that is permanently exposed to the vaginal cavity may cause undesired effects such as irritation to the vaginal tissue, excessive vaginal discharge, etc. Advantageously, in some embodiments, a proximal end of the securing element may be structured to prevent exposure of the thread, such as by a cover that shelters the thread. Alternately, the securing element may engage with the anchor using any other suitable means, such as via a mounting, a joint, and/or any other type of coupling. Optionally, the securing element and the proximal portion of the anchor may be structured such that the proximal portion of the anchor may fit within the securing element. The engagement may be employed pre- or post-release of the anchor from the elongated needle. Optionally, the engagement may be employed by tying, welding, gluing, clipping, fastening, crimping, or any other suitable mechanism.

Optionally, the securing element may be equipped with a triggerable actuator to prevent sliding of securing element over the thread in at least a one direction, thereby preventing a relative movement of the anchor. Optionally, the actuator of the securing element may be configured to exert force on the thread. Optionally, the actuator is a ratchet mechanism. In one non-limiting example, the securing element include inner teeth/ledges disposed around the thread and engageable with opposing teeth/ledges disposed on the thread. Optionally, the thread and the securing element include a snap-lock engagement mechanism formed there between for locking the thread and the securing element together. In one non-limiting example, the thread may include at least one protrusion and the securing element may include a complementary detent. Optionally, an alignment mechanism is formed between the thread and the securing element to rotationally align the thread and the securing element during sliding of the securing element over the thread.

Optionally, the securing element includes a bead and a thread fastening element. Non-limiting examples of beads and fastening elements are presented in FIGS. 7, 8A-B, 9A-B, 10A-B, 11, 12, and 13.

Reference is now made to FIG. 7 which shows a side view of a securing element 706 including a bead 706a and a knot 706b employed upon a thread 720 threaded through bead 706a to prevent a movement of bead 706a in at least one direction, in accordance with an embodiment.

Reference is now made to FIGS. 8A-B which show a side view and a proximal end view, respectively, of a securing element 806, in accordance with an embodiment. Securing element 806 operates as a friction ratchet mechanism. Securing element 806 includes an outer bead 806a and a fastening element 806b deployed within outer bead 806a. Fastening element 806b may include four tongues 806c extending inwardly from outer bead 806a towards one another to contact a thread 820, threaded through bead 806a, therebetween. Proximal movement of thread 820 is enabled, since four tongues 806c slide over the external surface of the thread. However, distal movement of thread 820 is prevented, because the edges of four tongues 806c lightly stab the thread, causing sufficient friction to prevent this distal movement.

Reference is now made to FIGS. 9A-B which show a side view and a proximal end view, respectively, of a securing element 906, in accordance with an embodiment. Securing element 906 operates as a friction ratchet mechanism. Securing element 906 includes an outer bead 906a and a fastening element 906b deployed within outer bead 906a. Fastening element 906b may include two tongues 906c extending inwardly from outer bead 906a towards one another to contact a thread 920, threaded through bead 906a, therebetween. Proximal movement of thread 920 is enabled, since two tongues 906c slide over the external surface of the thread. However, distal movement of thread 920 is prevented, because the edges of two tongues 906c lightly stab the thread, causing sufficient friction to prevent this distal movement.

Figure 10A:
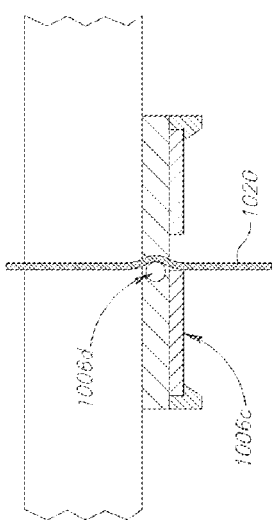
FIGS. 10A-10B are a side view and a proximal end view, respectively, of a securing element in accordance with an embodiment.
Figure 10B:
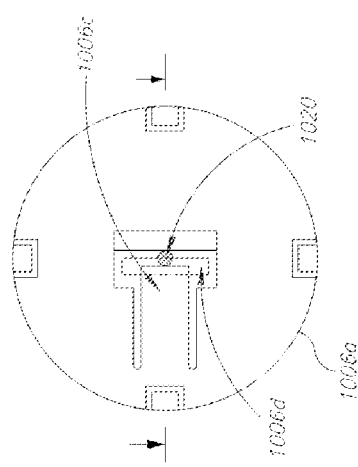

Reference is now made to FIGS. 10A-B which show a side view and a proximal end view, respectively, of a securing element 1006, in accordance with an embodiment. Securing element 1006 includes an outer bead 1006a and a fastening element 1006b deployed within outer bead 1006a. Fastening element may include a tongue 1006c and a pin 1006d. A thread 1020 may be threaded through a gap between pin 1006d and an inner surface of bead 1006a.

Optionally, tongue 1006c may push pin 1006d against a thread 1020, to secure thread 1020 between pin 1006d and an inner surface of bead 1006a.

Figure 11:
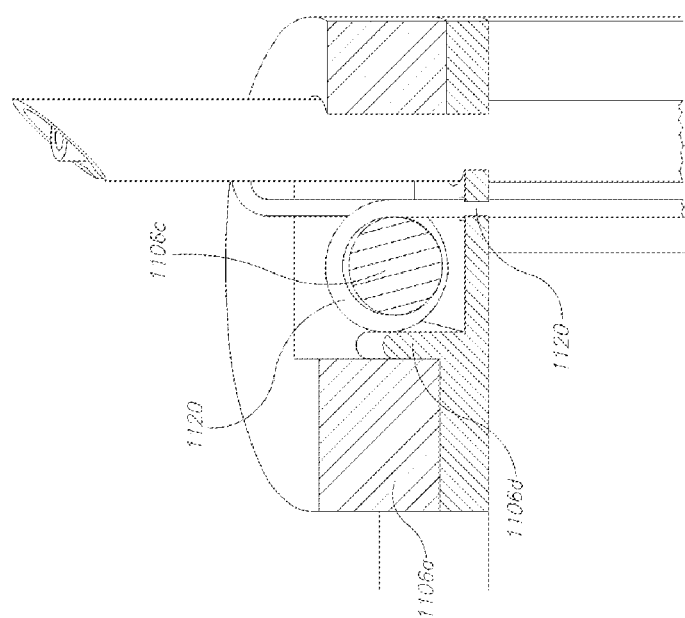
FIG. 11 shows a thread threaded through a securing element, in accordance with an embodiment.

Reference is now made to FIG. 11 which shows a thread 1120 threaded through a securing element 1106, in accordance with an embodiment. Securing element includes an outer bead 1006a and a fastening element 1006b including a protrusion 1106c and wedge 1106d. Thread 1120 may be wrapped around protrusion 1106c. Optionally, wedge 1106d may apply force and lock thread 1120 in place between protrusion 1106c and wedge 1106d.

Reference is now made to FIG. 12 which shows a thread 1220 threaded through an anchor 1208 and a bead 1206a of securing element 1206, in accordance with an embodiment. Thread 1220 may have a bulge at each of its ends, thereby to couple anchor 1208 and bead 1206a at a preset distance from one another.

Reference is now made to FIG. 13 which shows a thread 1320 threaded through an anchor 1308 and a securing element 1306, in accordance with an embodiment. Thread 1320 may have a bulge at each of its ends. Optionally, securing element 1306 includes a distal bead 1306a1 and a proximal bead 1306a2 coupled by a spring 1306b. Spring 1306b may act to make the interconnection of anchor 1308 and bead 1306 slightly resilient.

Optionally, the at least one hook is made of a superelastic material. As used herein, the term "superelastic" refers to the ability of a structure deformed under a load to return to its original configuration upon the removal of the load. The term "superelastic material" refers to the ability of a material to withstand at least twice as much strain as stainless steel materials can withstand without plastic deformation. Suitable superelastic materials may be biocompatible superelastic materials such as Nitinol (nickel-titanium alloy). As used herein, a material is biocompatible if the material and any degradation products of the material are generally nontoxic to a patient and possess no significant deleterious or untoward effects on the patient's body, such as a significant immunological reaction.

Optionally, at least two planar anchoring elements obtained from a sheet of a superelastic material may be coupled together to form the anchor. In some embodiments, the at least two planar anchoring elements are obtained by employing a technique selected from the group consisting of: stamping, cutting, molding, and forging. In some embodiments, a thickness of the sheet ranges from 0.1 mm to 1 mm, 0.2 mm to 1 mm, 0.3 mm to 1 mm, 0.4 mm to 1 mm, 0.5 mm to 1 mm, 0.6 mm to 1 mm, 0.1 mm to 0.9 mm, 0.2 mm to 0.9 mm, 0.3 mm to 0.9 mm, 0.4 mm to 0.9 mm, 0.5 mm to 0.9 mm, 0.6 mm to 0.9 mm, 0.1 mm to 0.8 mm, 0.2 mm to 0.8 mm, 0.3 mm to 0.8 mm, 0.4 mm to 0.8 mm, 0.5 mm to 0.8 mm, 0.6 mm to 0.8 mm, 0.1 mm to 0.7 mm, 0.2 mm to 0.7 mm, 0.3 mm to 0.7 mm, 0.4 mm to 0.7 mm, 0.5 mm to 0.7 mm, 0.6 mm to 0.7 mm, 0.1 mm to 0.6 mm, 0.2 mm to 0.6 mm, 0.3 mm to 0.6 mm, 0.4 mm to 0.6 mm, or 0.5 mm to 0.6 mm. Each possibility represents a separate embodiment of the present invention. The different embodiments can be combined at will.

Optionally, the at least two planar anchoring elements may be structured to fit together such as by employing a latching mechanism. Alternatively, the at least two planar anchoring elements may be coupled together by welding, gluing, clipping, crimping, or any other appropriate coupling mechanism.

In some embodiments, the anchor includes two planar anchoring elements coupled together. In such embodiments, the planes of the two planar anchoring elements define an angle ranging from 5° to 175°, 10° to 170°, 15° to 165°, 20° to 160°, 25° to 155°, 30° to 150°, 35° to 145°, 40° to 140°, 45° to 135°, 50° to 130°, 55° to 125°, 60° to 120°, 65° to 115°, 70° to 110°, 75° to 105°, 80° to 100°, 85° to 95° between them. Each possibility represents a separate embodiment of the present invention. The different embodiments can be combined at will. In some embodiments, the planes of the two planar anchoring elements are perpendicular to one another.

A person skilled in the art would appreciate that the dimensions of the apparatus and its components may vary according to the target tissues to be affixed. In some embodiments, the apparatus is for affixing a first tissue to a second tissue within a body cavity. In some embodiments, the body cavity is a vaginal cavity. In some embodiments, the apparatus is for affixing a vaginal wall to the sacrospinous ligament.

Throughout the following description, similar elements of different embodiments of the apparatus are referenced by element numbers differing by integer multiples of 100. For example, a superelastic anchor of FIG. 1 is referenced by the number 108, and a superelastic anchor of FIG. 2, which corresponds to superelastic anchor 108, is referenced by the number 208.

Figure 1B:
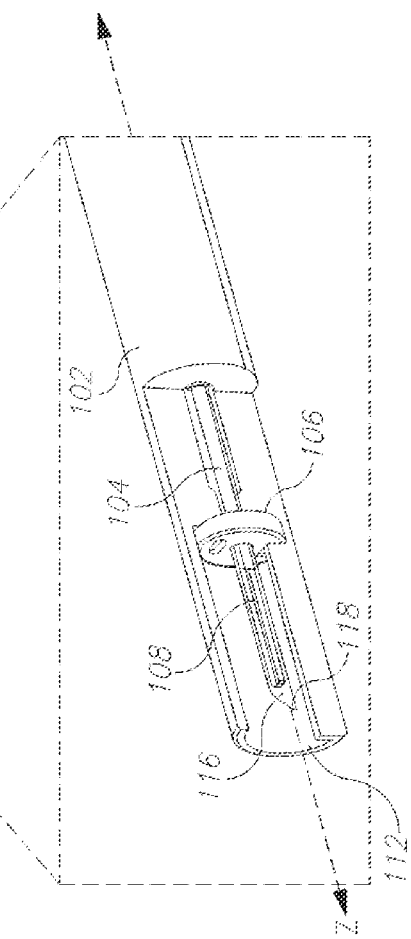
FIG. 1B shows an enlarged, partially transparent view of a distal portion of a shaft of the apparatus of FIG. 1A, in accordance with an embodiment.
Figure 1C:
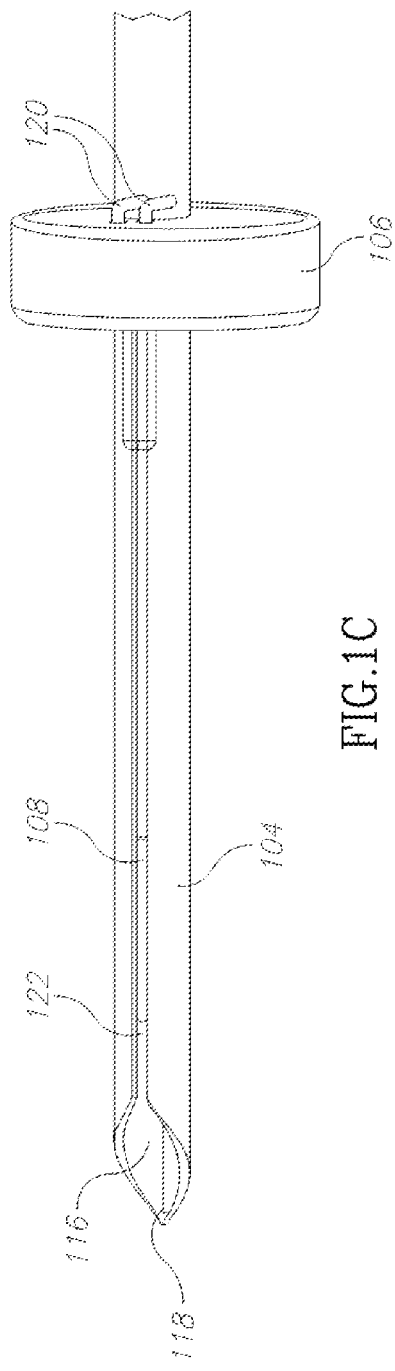
FIG. 1C shows a perspective view of an elongated needle and a securing element of the apparatus of FIG. 1A, in accordance with an embodiment.
Figure 1D:
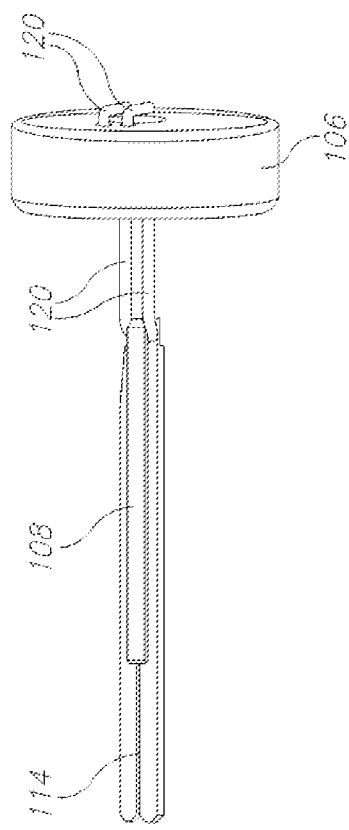
FIG. 1D shows a perspective view of the securing element of FIG. 1C and a superelastic anchor of the apparatus of FIG. 1A in its contracted configuration, in accordance with an embodiment.
Figure 1E:
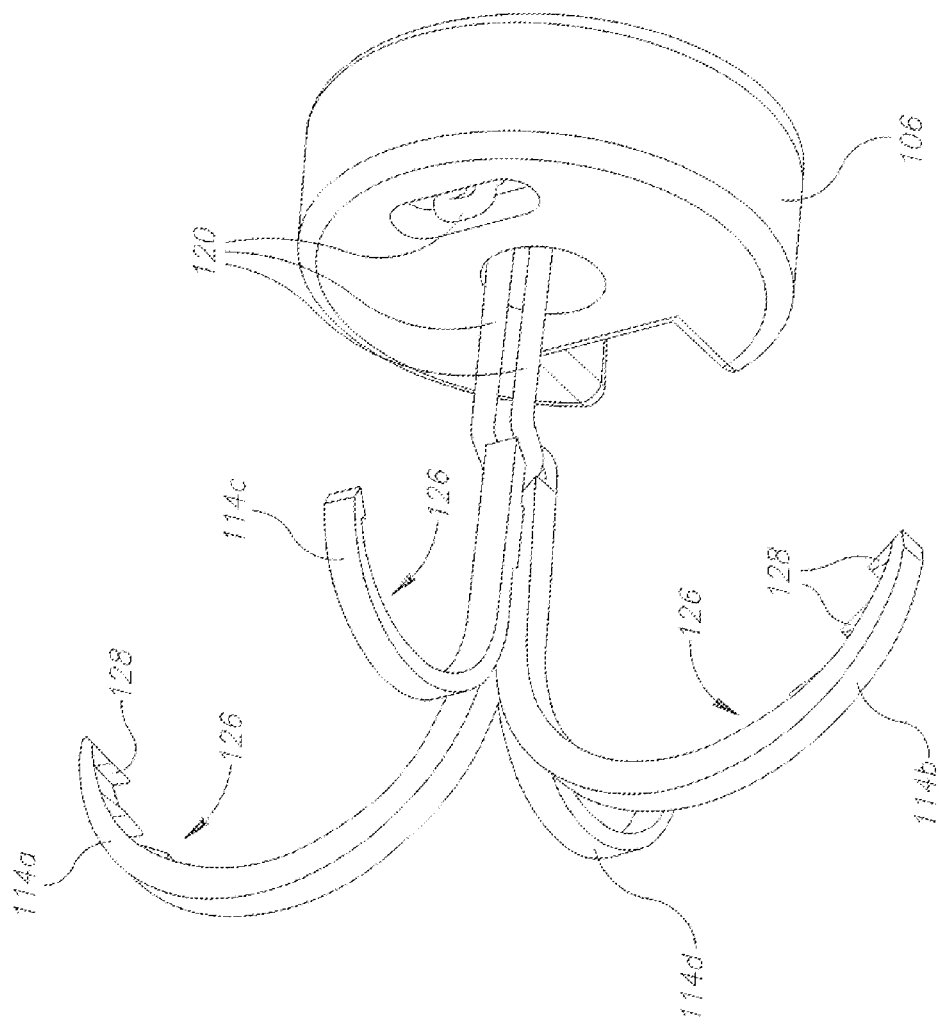
FIG. 1E shows a perspective view of the securing element of FIG. 1C and the superelastic anchor of FIG. 1D in its expanded configuration, following release from the apparatus of FIG. 1A, in accordance with an embodiment.

Reference is now made to FIGS. 1A, 1B, 1C, 1D and 1E, which show an apparatus 100 that may be used for affixing a first tissue to a second tissue. FIG. 1A shows a fully assembled view of apparatus 100, in accordance with an embodiment. FIG. 1B shows an enlarged partially transparent view of a distal portion of a shaft 102 of apparatus 100 showing an elongated needle ('needle') 104 and a securing element 106 disposed within shaft 102, in accordance with an embodiment. FIG. 1C is a perspective view showing needle 104 and securing element 106 of apparatus 100, in accordance with an embodiment. FIG. 1D is a perspective view showing securing element 106 and a superelastic anchor ('anchor') 108 in its contracted configuration, in accordance with an embodiment. FIG. 1E is a perspective view showing securing element 106 and an anchor 108 in its expanded configuration following release from needle 104, in accordance with an embodiment.

To facilitate the description of apparatus 100, a longitudinal axis Z is indicated in FIGS. 1A-B and refers to a central axis that extends along the length of shaft 102 of apparatus 100 from a proximal end 110 to a distal opening 112.

Apparatus 100 includes needle 104 housing anchor 108 which includes at least one normally-expanded elongated hook ('at least one hook') 114 that is biased to a contracted state to fit within elongated needle 104. Optionally, anchor 108 may be released from needle 104 via a distal opening 116. Optionally, anchor 108 may be released within a tissue. Optionally, upon release of anchor 108 from needle 106, at least one hook 114 may extend distally outward from the longitudinal axis of needle 104. Optionally, at least one hook 114 may include a pair of opposing hooks 114a and 114b and a pair of opposing hooks 114c and 114d in a perpendicular relation. Optionally, an inner surface 126 of at least one hook 114 is further equipped with teeth 128 to engage with a tissue and provide better hold of the tissue.

Optionally, needle 104 is further equipped with a distal piercing tip 118 (e.g., a sharp, beveled edge) to pierce and penetrate a tissue (e.g., vaginal wall, and sacrospinous ligament). In a non-limiting example, needle 104 pierces and penetrates the vaginal wall and the sacrospinous ligament and anchor 108 is released within the sacrospinous ligament.

Alternatively, piercing tip 118 may penetrates a body cavity through a tissue and anchor 108 may be released in that body cavity.

Optionally, apparatus 100 further includes securing element 106 structured to couple with a proximal end of anchor 108. Optionally, securing element 106 and anchor 108 are coupled via a thread 120. Optionally, thread 120 extends from securing element 106 and anchor 108 via an elongated slot 122 disposed along at least a distal portion of a length of needle 104. Optionally, thread 120 is threaded through at least one of securing element 106 and anchor 108.

Optionally, needle 104 and securing element 106 are disposed within shaft 102. Optionally, securing element 106 may be slidably disposed around needle 104. Alternatively, securing element may be disposed separately such as, for a non-limiting example, from another shaft (not shown). Optionally, at least one of needle 104 and securing element 106 may be advanced out from shaft 102 through distal opening 112 such as by employing an advancement mechanism (not shown). Upon advancement, securing element 106 may be released from shaft 102. Upon advancement, needle 104 may protrude distally from shaft 102 in order to sequentially pierce a first tissue and penetrate a second tissue. A person with skill in the art would appreciate that a preset maximal distance between distal opening 116 of needle 104 and distal opening 112 of shaft 102 may range according to the first and second target tissues. In some embodiments, the preset distance ranges from 5 mm to 20 mm, 7 mm to 20 mm, 5 mm to 15 mm, 6 mm to 15 mm, 7 mm to 15 mm, 8 mm to 15 mm, 9 mm to 15 mm, 10 mm to 15 mm, 5 mm to 13 mm, 6 mm to 13 mm, 7 mm to 13 mm, 8 mm to 13 mm, 9 mm to 13 mm, 10 mm to 13 mm, 5 mm to 11 mm, 6 mm to 11 mm, 7 mm to 11 mm, 8 mm to 11 mm, 9 mm to 11 mm, 10 mm to 11 mm, 5 mm to 9 mm, 6 mm to 9 mm, 7 mm to 9 mm, 8 mm to 9 mm, 5 mm to 8 mm, 6 mm to 8 mm, or 7 mm to 8 mm. Each possibility represents a separate embodiment of the present invention. The different embodiments can be combined at will.

Optionally, apparatus 100 is further equipped with a handle 124 disposed at a proximal end of needle 104. Optionally, handle 124 is coupled to proximal end 110 of shaft 102 in a fixed or alternatively a detachable manner. Handle 124 may be configured to trigger an advancement mechanism (not shown) to eject anchor 108 out of distal opening 116 of needle 104 to allow at least one hook 114 to extend distally outward from the longitudinal axis of needle 104, and further eject securing element 106 from shaft 102, to prevent a proximal movement of anchor 108 relative to securing element 106. Optionally, securing element 106 is equipped with an actuator (not shown) triggerable to prevent sliding of securing element 106 over thread 120 in at least a one direction thereby preventing a relative movement of anchor 108. Optionally, the actuator of securing element 106 is configured to exert force on thread 120. Optionally, securing element 106 and thread 120 engage by a ratchet mechanism which allows one directional sliding of securing element 106 over thread 120.

Figure 2A:
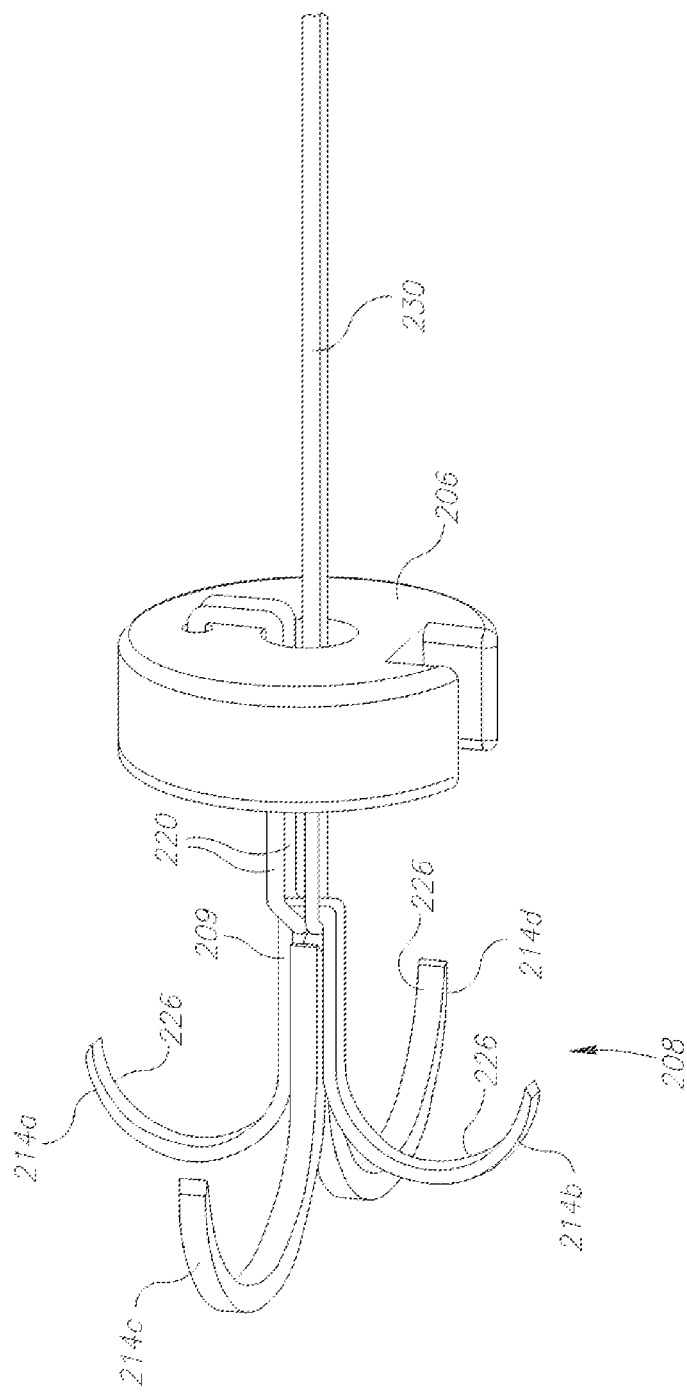
FIG. 2A shows a perspective view of a securing element and a superelastic anchor in its expanded configuration, following release from an apparatus for affixing a first tissue to a second tissue, in accordance with an embodiment.

Reference is now made to FIG. 2A which shows a perspective view of an anchor 208 and a securing element 206 of an apparatus 200 that may be used for affixing a first tissue to a second tissue, in accordance with another embodiment.

Anchor 208 is substantially similar to apparatus 100 described in FIGS. 1A-E with the notable difference of the inner surfaces 226 of hooks 214a, 214b, 214c and 214d being substantially smoother such that teeth 128 of FIG. 1A are not present, to allow retrieval of anchor 208. Optionally, anchor 208 may be further coupled with a retrieving wire 230. Optionally, retrieving wire 230 is coupled to a proximal base 209 of anchor 208. Optionally, anchor 208 may be detached from securing element 206 by cutting a thread 220 which couples anchor 208 and securing element 206. Optionally, thread 220 is coupled to proximal base 209 of anchor 208. Optionally, retrieving wire 230 may be pulled in a proximal direction to retrieve anchor 208. Optionally, retrieving wire 230 may be pulled in a proximal direction following detachment of securing element 206 from anchor 208.

A person skilled in the art will appreciate that retrieval of an anchor 208 deployed within a tissue by pulling the anchor in a proximal direction may induce damage (e.g., rupture) to the tissue resulting from movement of hooks 214a, 214b, 214c and 214d relative to the tissue. Advantageously, in order to retrieve anchor 208 deployed within a tissue without damaging the tissue, anchor 208 may be first contracted to fit within a retrieval device and then retrieved from the tissue within the retrieval device. In a non-limiting example, anchor 208 deployed within the sacrospinous ligament may be retrieved through the vaginal wall via a retrieval device which prevents direct contact between anchor 208 and the vaginal wall.

Figure 2B:
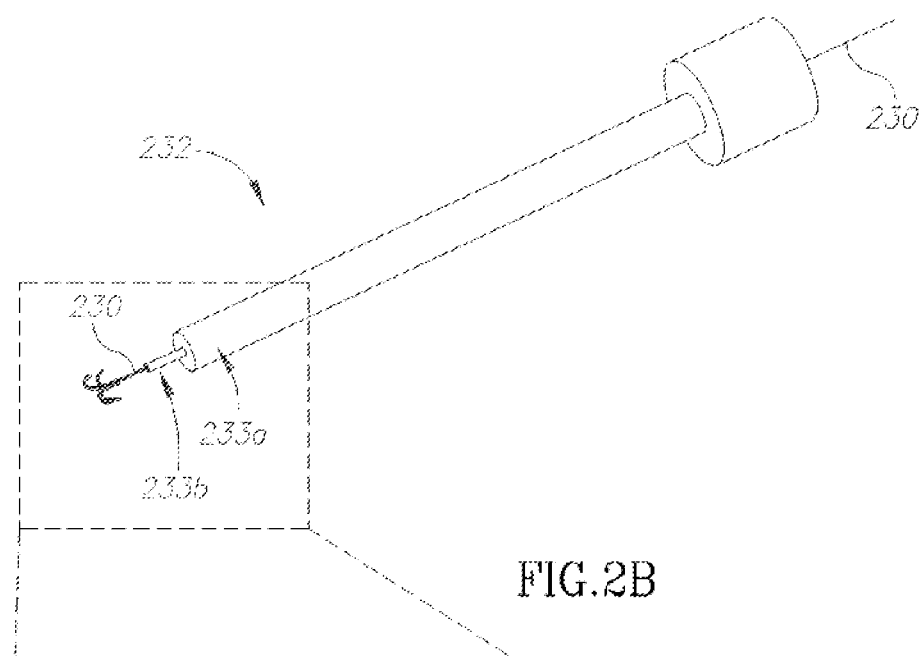
FIG. 2B shows the anchor of FIG. 2A in position to be pulled into a retrieval device, in accordance with an embodiment.
Figure 2C:
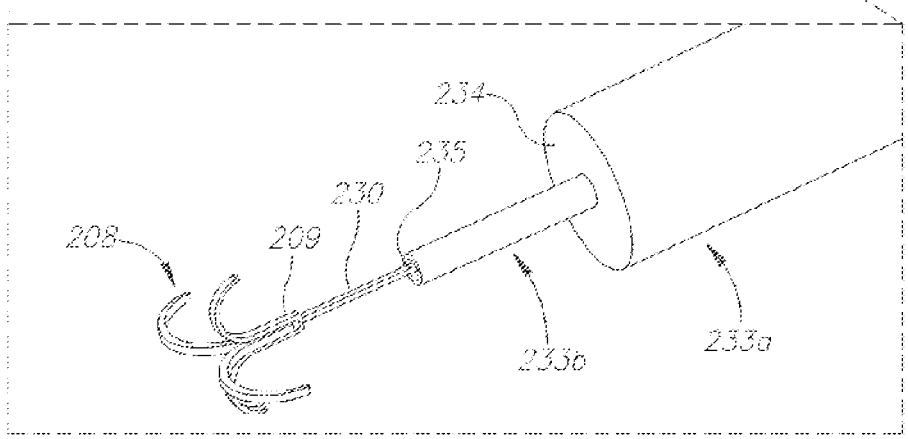
FIG. 2C shows an enlarged view of FIG. 2B, in accordance with an embodiment.

Reference is now made to FIGS. 2B-C which show a perspective view of anchor 208 of apparatus 200 pulled into a retrieval device 232, in accordance with an embodiment. Retrieval device 232 includes a penetrating tube 233b having a distal opening 235 through which anchor 208 may be pulled into penetrating tube 233b. The inner diameter of penetrating tube 233b is optionally slightly larger than the outer diameter of anchor 208, when collapsed. For example, the inner diameter of penetrating tube 233b may be 1-5%, 5-10%, 10-15%, or more than 15% larger than the outer diameter of anchor 208 when collapsed.

Optionally, penetrating tube 233b has a distal piercing tip (not shown) to penetrate a tissue and allow positioning of distal opening 235 adjacent to proximal base 209 of anchor 208. Optionally, penetrating tube 233b of retrieval device 232 is disposed around and advanced distally along the length of retrieving wire 230 to allow distal opening 235 of penetrating tube 233b to reach the base of anchor 208. Retrieving wire 230 may be pulled through penetrating tube 233b of retrieval device 232 to facilitate insertion of the proximal base of anchor 208 into catheter 233b via distal opening 235. Anchor 208 may contract upon proximal advancement through penetrating tube 233b to fit within penetrating tube 233b. Optionally, retrieval device 232 further includes a second tube 233a disposed coaxially around penetrating tube 233b. Optionally, penetrating tube 233b protrudes distally from distal end 234 (e.g., distal opening) of second tube 233a. Optionally, the protrusion of penetrating tube 233b from distal end 234 is facilitated by advancement of penetrating tube 233b along the longitudinal axis within second tube 233a.

Figure 2D:
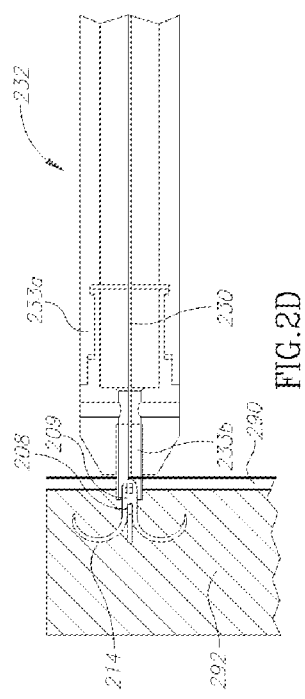
FIGS. 2D-2F are schematic illustrations, each illustrating a step of a method for retrieving an anchor deployed in a ligament through a vaginal wall, in accordance with the anchor and retrieval device of FIGS. 2B-C.
Figure 2E:
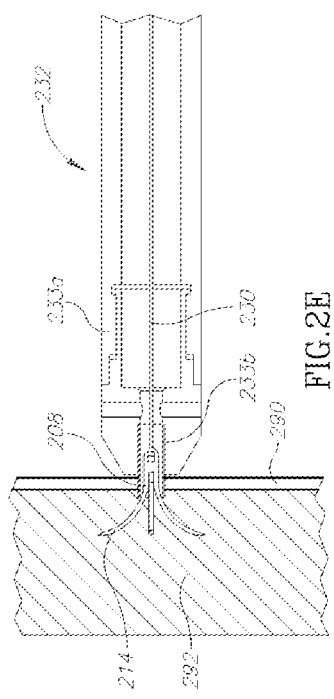
Figure 2F:
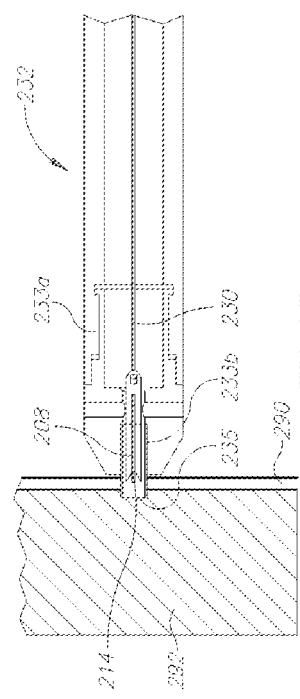

Reference is now made to FIGS. 2D-F each illustrating a step of a method for employing retrieval device 232 to retrieve anchor 208 deployed within a second tissue (e.g., sacrospinous ligament) 292 through a first tissue (e.g., vaginal wall) 290 without exposing hooks 214a, 214b, 214c, 214d to first tissue 290. Reference is now made to FIG. 2D which shows second tube 232 introduced against a proximal surface of first tissue 290 and distal opening 235 of penetrating tube 233b enclosing on proximal base 209 of anchor 208 within second tissue 292. Optionally, penetrating tube 233b sequentially penetrates through first tissue 290 into second tissue 292 with the distal piercing tip to reach proximal base 209 of anchor 208.

Reference is now made to FIG. 2E which shows a partially contracted configuration of hooks 214 contracted to fit within penetrating tube 233b upon proximal advancement of anchor 208 through penetrating tube 233b. Reference is now made to FIG. 2F which shows anchor 208 in its contracted configuration within penetrating tube 233b.

Figure 2G:
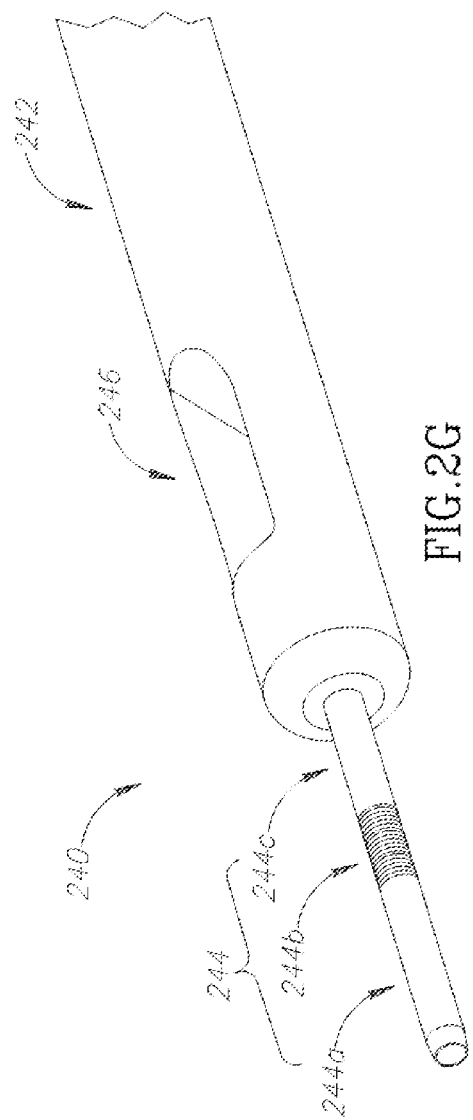
FIGS. 2G-2H are perspective and cross-sectional views, respectively, of a retrieval device, in accordance with an embodiment.
Figure 2H:
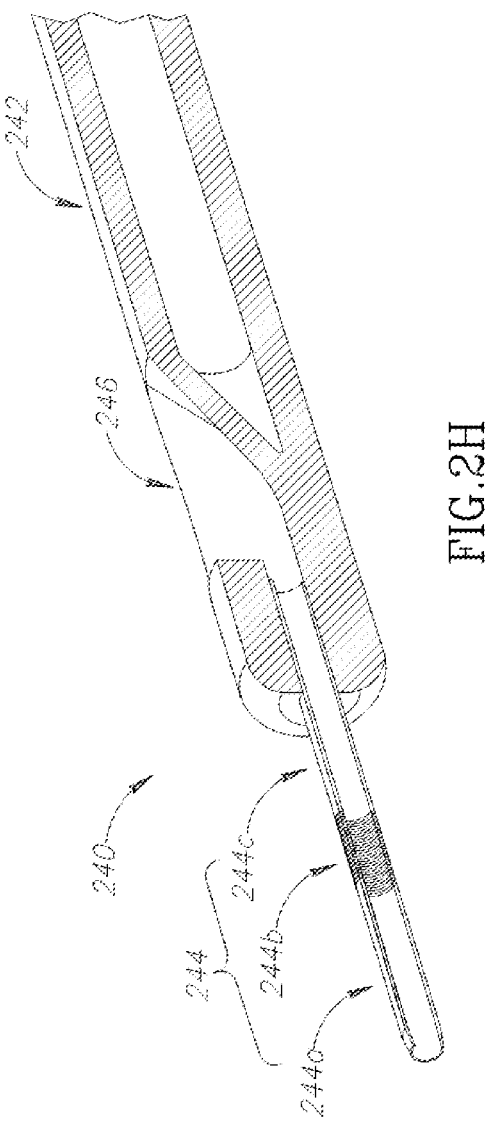
Figure 3A:
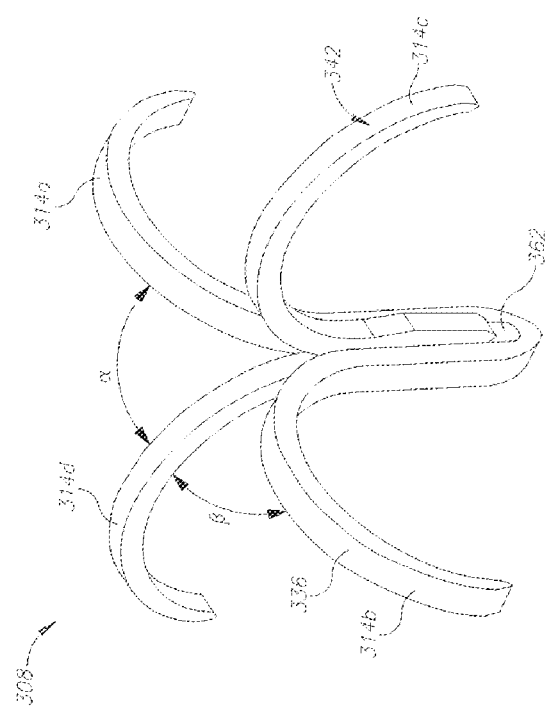
FIG. 3A shows a fully assembled view of an anchor, in accordance with an embodiment.

FIGS. 2G-2H are perspective and cross-sectional views, respectively, of an alternative retrieval device 240, in accordance with an embodiment. Retrieval device 240 includes an elongated shaft 242, only the distal portion thereof is visible in these figures. Shaft 242 optionally has a lateral opening 246 that is internally connected to a distal opening of the shaft.

A handle (not shown) may also be part of retrieval device 240, and be disposed at the proximal side of shaft 242. The handle may include a grip allowing the surgeon to conveniently hold and operate retrieval device 240. Shaft 242 may be long enough, such that, when its distal end reaches the sacrospinous ligament, its handle remains completely or mostly outside the patient's vaginal opening. The handle may also include a thread pulling mechanism, that enables securing the free end of the thread (that is connected to the base on the anchor) to the handle, and pulling of the thread from there. For example, the thread pulling mechanism may include a pulley, over which the thread may be wound.

A flexible tube 244 emerges from the distal opening of shaft 242, and is optionally structured of three parts: a proximal rigid tube 244c that is attached to, connected to, or integrally formed with shaft 242; a flexible joint, such as a coiled spring 244b, and a distal rigid tube (or needle) 244a that has a distal opening, optionally sharpened. Those of skill in the art will recognize that a flexible tube may be structured differently, as long as it is configured to operate in the manner described below.

Retrieval device 240 operates as follows: The free end of the thread, that is connected to the base of the anchor, and is optionally long enough to emerge from the vaginal opening, is inserted by the surgeon into the distal opening of flexible tube 244, and threaded through the flexible tube until it emerges from lateral opening 246 of shaft 242.

Then, the free end of the thread may be pulled proximally, relative to retrieval device 240. This may be performed by activating the thread pulling mechanism at the handle, which, for example, wounds the thread over a pulley and causes a shortening of the distance between the anchor and retrieval device 240 by rotating the pulley. Since the force securing the anchor to the tissue is relatively strong, retrieval device 240, in effect, will be pulled towards the anchor, and the distal opening of flexible tube 244 will penetrate the tissue (e.g., the vaginal wall and then the sacrospinous ligament), and, next, encircle the base of the anchor.

The flexibility of flexible tube 244, achieved by the coiled spring 244b (or by a different flexible mechanism), self-guides to encircle the base of the anchor. Namely, flexible tube 244 slides over the thread, which is kept taut as retrieval device 240 advances distally, and the flexible tube can flex in any radial dimension until it encircles the anchor base.

Flexible tube 244 may be advanced (e.g., by pulling the thread towards retrieval device 240) until, for example, its distal opening reaches an area where the hooks of the anchor begin to curl outwardly. Then, the surgeon may keep retrieval device 240 in place, while continuing to pull the thread distally. This will cause the anchor's hooks to gradually collapse as the anchor is withdrawn into flexible tube 244.

The inner diameter of flexible tube 244 (or of at least a distal portion thereof which is sufficiently long to house the collapsed anchor) is optionally slightly larger than the outer diameter of the anchor, when collapsed. For example, the inner diameter of flexible tube 244 may be 1-5%, 5-10%, 10-15%, or more than 15% larger than the outer diameter of the anchor when collapsed.

Optionally, flexible tube 244 has an anchor delimiter inside its lumen, which prevents the anchor from sliding proximally through the entire flexible tube and out of lateral opening 246. In some scenarios, it may be beneficial to ensure that the anchor stays secured to flexible tube 244 until retrieval device 240 is completely extracted from the body. The anchor delimiter may be embodied, for example, by a narrower inner diameter of coiled spring 244b, which is narrower than the outer diameter of the collapsed anchor. This will maintain the anchor inside distal rigid tube 244a and prevent its migration further proximally. Another option is to include an internal protrusion (not shown) inside the flexible tube, which stops the anchor from moving past it.

Reference is now made to FIGS. 3A-E which show multiple views of a superelastic anchor ('anchor') 208 that may be used in apparatus 100 for affixing a first tissue to a second tissue, in accordance with an embodiment.

Reference is now made to FIGS. 3A-E which show multiple views of a superelastic anchor ('anchor') 308 that may be used in apparatus 100 of FIGS. 1A-E for affixing a first tissue to a second tissue, in accordance with an embodiment. FIGS. 3A, 3B, 3C, 3D, and 2E show a fully assembled view of anchor 308 including a first planar anchoring element 336 and a second planar anchoring element 342, a perspective view showing first planar anchoring element 336 of anchor 308, a distal end view showing a thickness 364 of first planar anchoring element 336, a perspective view showing second planar anchoring element 342 of anchor 308, and a distal end view showing a thickness 366 of second planar anchoring element 342, respectively.

To facilitate the description of first planar anchoring element 336 and second planar anchoring element 342, three orthogonal axes are indicated in FIGS. 3B and 3C. Referring to FIG. 3B, the axis labelled 'longitudinal axis' refers to a central axis that extends along the length of a first proximal coupling portion 344 of first planar anchoring element 336 from a proximal end 346 of first planar anchoring element 336 to a distal end 348. The axis labelled 'lateral axis' indicates the width of first planar anchoring element 336 and extends from a first lateral edge 350a of a distal pair of opposing hooks 314a and 314b of first planar anchoring element 336 to a second lateral edge 350b of a distal pair of opposing hooks 314a and 314b of first planar anchoring element 336. The axis labelled 'vertical axis' extends from an anterior side to a posterior side of first planar anchoring element 336 defining the thickness of first planar anchoring element 336, and is perpendicular to both the vertical and the longitudinal axes. Referring to FIG. 3D, the axis labelled 'longitudinal axis' refers to a central axis that extends along the length of a second proximal coupling portion 352 of second planar anchoring element 342 from a proximal end 354 to a distal end 356. The axis labelled 'lateral axis' indicates the width of first planar anchoring element 342 and extends from a first lateral edge 350c of a distal pair of opposing hooks 314c and 314d of second planar anchoring element 342 to a second lateral edge 350d of distal pair of opposing hooks 314c and 314d of second planar anchoring element 342. The axis labelled 'vertical axis' extends from an anterior side to a posterior side of second planar anchoring element 342 defining the thickness of second planar anchoring element 342, and is perpendicular to both the vertical and the longitudinal axes.

Anchor 308 includes a first planar anchoring element 336 and a second planar anchoring element 342. Optionally, first planar anchoring element 336 of anchor 308 and second planar anchoring element 342 of anchor 308 may be coupled together such that their planes define a first angle α and a supplementary angle β between them. In some embodiments, first angle α ranges between 30° to 150° and supplementary angle β is a supplementary angle to first angle α. Optionally, the planes of first planar anchoring element 336 of anchor 308 and second planar anchoring element 342 of anchor 308 may be substantially perpendicular to one another. Optionally, first and second planar anchoring elements 336 and 342 are structured to couple together upon insertion and latching of proximal protrusions 358a and 360a of second planar anchoring element 342 to an aperture 362 of first planar anchoring element 336.

First planar anchoring element 336 may include first proximal coupling portion 344, and a distal pair of opposing hooks 314a and 314b which are disposed co-planarly with and extend distally and laterally away from first proximal coupling portion 344. Optionally, first proximal coupling portion 344 includes an aperture 362 extending between a posterior side and an anterior side of first proximal coupling portion 344.

Optionally, each of hooks 314a and 314b define an inner curvature having a radius R1. In some embodiments radius R1 ranges from 2 mm to 3 mm, 2.1 mm to 3 mm, 2.2 mm to 3 mm, 2.3 mm to 3 mm, 2.4 mm to 3 mm, 2.5 mm to 3 mm, 2 mm to 2.6 mm, 2.1 mm to 2.6 mm, 2.2 mm to 2.6 mm, 2.3 mm to 2.6 mm, 2.4 mm to 2.6 mm, 2 mm to 2.5 mm, 2.1 mm to 2.5 mm, 2.2 mm to 2.5 mm, 2.3 mm to 2.5 mm, 2.4 mm to 2.5 mm, 2 mm to 2.4 mm, 2.1 mm to 2.4 mm, 2.2 mm to 2.4 mm, or 2.3 mm to 2.4 mm. Each possibility represents a separate embodiment of the present invention. The different embodiments can be combined at will.

Optionally, first lateral edge 350a and second lateral edge 350b of hooks 314a and 314b, respectively, may taper along the plane defined by the longitudinal-lateral axes, resulting in a pointed surface on the proximal edge of each of first lateral edge 350a and second lateral edge 350b.

In some embodiments, a width 337 measured from first lateral edge 350a to second lateral edge 350b of distal pair of opposing hooks 314a and 314b of first planar anchoring element 336 ranges from 4 mm to 16 mm, 4 mm to 15 mm, 4 mm to 14 mm, 4 mm to 13 mm, 4 mm to 12 mm, 4 mm to 10 mm, 4 mm to 9 mm, 4 mm to 8 mm, 4 mm to 7 mm, 4 mm to 6.5 mm, 4 mm to 6 mm, 8 mm to 12.4 mm, 8 mm to 12.2 mm, 8 mm to 12.1 mm, 8 mm to 12 mm, 8 mm to 11.9 mm, 8 mm to 11.8 mm, 8 mm to 11.7 mm, 8 mm to 11.6 mm, 8 mm to 11.5 mm, 8 mm to 11.4 mm, 8 mm to 11.3 mm, 8 mm to 11.2 mm, 8.5 mm to 13 mm, 8.5 mm to 12.9 mm, 8.5 mm to 12.8 mm, 8.5 mm to 12.7 mm, 8.5 mm to 12.6 mm, 8.5 mm to 12.5 mm, 8.5 mm to 12.4 mm, 8.5 mm to 12.2 mm, 8.5 mm to 12.1 mm, 8.5 mm to 12 mm, 8.5 mm to 11.9 mm, 8.5 mm to 11.8 mm, 8.5 mm to 11.7 mm, 8.5 mm to 11.6 mm, 8.5 mm to 11.5 mm, 8.5 mm to 11.4 mm, 8.5 mm to 11.3 mm, 8.5 mm to 11.2 mm, 9 mm to 13 mm, 9 mm to 12.9 mm, 9 mm to 12.8 mm, 9 mm to 12.7 mm, 9 mm to 12.6 mm, 9 mm to 12.5 mm, 9 mm to 12.4 mm, 9 mm to 12.2 mm, 9 mm to 12.1 mm, 9 mm to 12 mm, 9 mm to 11.9 mm, 9 mm to 11.8 mm, 9 mm to 11.7 mm, 9 mm to 11.6 mm, 9 mm to 11.5 mm, 9 mm to 11.4 mm, 9 mm to 11.3 mm, 9 mm to 11.2 mm, 9.5 mm to 13 mm, 9.5 mm to 12.9 mm, 9.5 mm to 12.8 mm, 9.5 mm to 12.7 mm, 9.5 mm to 12.6 mm, 9.5 mm to 12.5 mm, 9.5 mm to 12.4 mm, 9.5 mm to 12.2 mm, 9.5 mm to 12.1 mm, 9.5 mm to 12 mm, 9.5 mm to 11.9 mm, 9.5 mm to 11.8 mm, 9.5 mm to 11.7 mm, 9.5 mm to 11.6 mm, 9.5 mm to 11.5 mm, 9.5 mm to 11.4 mm, 9.5 mm to 11.3 mm, 9.5 mm to 11.2 mm, 10 mm to 13 mm, 10 mm to 12.9 mm, 10 mm to 12.8 mm, 10 mm to 12.7 mm, 10 mm to 12.6 mm, 10 mm to 12.5 mm, 10 mm to 12.4 mm, 10 mm to 12.2 mm, 10 mm to 12.1 mm, 10 mm to 12 mm, 10 mm to 11.9 mm, 10 mm to 11.8 mm, 10 mm to 11.7 mm, 10 mm to 11.6 mm, 10 mm to 11.5 mm, 10 mm to 11.4 mm, 10 mm to 11.3 mm, 10 mm to 11.2 mm, 10.5 mm to 13 mm, 10.5 mm to 12.9 mm, 10.5 mm to 12.8 mm, 10.5 mm to 12.7 mm, 10.5 mm to 12.6 mm, 10.5 mm to 12.5 mm, 10.5.5 mm to 12.4 mm, 10.5 mm to 12.2 mm, 10.5 mm to 12.1 mm, 10.5 mm to 12 mm, 10.5 mm to 11.9 mm, 10.5 mm to 11.8 mm, 10.5 mm to 11.7 mm, 10.5 mm to 11.6 mm, 10.5 mm to 11.5 mm, 10.5 mm to 11.4 mm, 10.5 mm to 11.3 mm, 10.5 mm to 11.2 mm, 11 mm to 13 mm, 11 mm to 12.9 mm, 11 mm to 12.8 mm, 11 mm to 12.7 mm, 11 mm to 12.6 mm, 11 mm to 12.5 mm, 11 mm to 12.4 mm, 11 mm to 12.2 mm, 11 mm to 12.1 mm, 11 mm to 12 mm, 11 mm to 11.9 mm, 11 mm to 11.8 mm, 11 mm to 11.7 mm, 11 mm to 11.6 mm, 11 mm to 11.5 mm, 11 mm to 11.4 mm, 11 mm to 11.3 mm, or 11 mm to 11.2 mm. Each possibility represents a separate embodiment of the present invention. The different embodiments can be combined at will.

In some embodiments, a width 338 of hooks 314a and 314b ranges from 0.2 mm to 0.6 mm, 0.2 mm to 0.58 mm, 0.2 mm to 0.56 mm, 0.2 mm to 0.54 mm, 0.2 mm to 0.52 mm 0.2 mm to 0.5 mm, 0.2 mm to 0.48 mm, 0.2 mm to 0.46 mm, 0.2 mm to 0.44 mm, 0.2 mm to 0.42 mm, 0.2 mm to 0.41 mm, 0.2 mm to 0.40 mm, 0.2 mm to 0.39 mm, 0.25 mm to 0.6 mm, 0.25 mm to 0.58 mm, 0.25 mm to 0.56 mm, 0.25 mm to 0.54 mm, 0.25 mm to 0.52 mm 0.25 mm to 0.5 mm, 0.25 mm to 0.48 mm, 0.25 mm to 0.46 mm, 0.25 mm to 0.44 mm, 0.25 mm to 0.42 mm, 0.25 mm to 0.41 mm, 0.25 mm to 0.40 mm, 0.25 mm to 0.39 mm, 0.3 mm to 0.6 mm, 0.3 mm to 0.58 mm, 0.3 mm to 0.56 mm, 0.3 mm to 0.54 mm, 0.3 mm to 0.52 mm 0.3 mm to 0.5 mm, 0.3 mm to 0.48 mm, 0.3 mm to 0.44 mm, 0.3 mm to 0.42 mm, 0.3 mm to 0.41 mm, 0.3 mm to 0.40 mm, 0.3 mm to 0.39 mm, 0.32 mm to 0.6 mm, 0.32 mm to 0.58 mm, 0.32 mm to 0.56 mm, 0.32 mm to 0.54 mm, 0.32 mm to 0.52 mm 0.32 mm to 0.5 mm, 0.32 mm to 0.48 mm, 0.32 mm to 0.44 mm, 0.32 mm to 0.42 mm, 0.32 mm to 0.41 mm, 0.32 mm to 0.40 mm, 0.32 mm to 0.39 mm, 0.34 mm to 0.6 mm, 0.34 mm to 0.58 mm, 0.34 mm to 0.56 mm, 0.34 mm to 0.54 mm, 0.34 mm to 0.52 mm 0.34 mm to 0.5 mm, 0.34 mm to 0.48 mm, 0.34 mm to 0.44 mm, 0.34 mm to 0.42 mm, 0.34 mm to 0.41 mm, 0.34 mm to 0.40 mm, 0.34 mm to 0.39 mm, 0.36 mm to 0.6 mm, 0.36 mm to 0.58 mm, 0.36 mm to 0.56 mm, 0.36 mm to 0.54 mm, 0.36 mm to 0.52 mm 0.36 mm to 0.5 mm, 0.36 mm to 0.48 mm, 0.36 mm to 0.44 mm, 0.36 mm to 0.42 mm, 0.36 mm to 0.41 mm, 0.36 mm to 0.40 mm, 0.36 mm to 0.39 mm, 0.37 mm to 0.6 mm, 0.37 mm to 0.58 mm, 0.37 mm to 0.56 mm, 0.37 mm to 0.54 mm, 0.37 mm to 0.52 mm 0.37 mm to 0.5 mm, 0.37 mm to 0.48 mm, 0.37 mm to 0.44 mm, 0.37 mm to 0.42 mm, 0.37 mm to 0.41 mm, 0.37 mm to 0.40 mm, or 0.37 mm to 0.39 mm. Each possibility represents a separate embodiment of the present invention. The different embodiments can be combined at will.

In some embodiments, a height 339 measured along the longitudinal axis from proximal end 346 to a distal end of hook 314a or 314b ranges from 4 mm to 16 mm, 4 mm to 15 mm, 4 mm to 14 mm, 4 mm to 13 mm, 4 mm to 12 mm, 4 mm to 10 mm, 4 mm to 9 mm, 4 mm to 8 mm, 4 mm to 7 mm, 4 mm to 6.5 mm, 4 mm to 6 mm, 5 mm to 16 mm, 5 mm to 15 mm, 5 mm to 14 mm, 5 mm to 13 mm, 5 mm to 12 mm, 5 mm to 10 mm, 5 mm to 9 mm, 5 mm to 8 mm, 5 mm to 7 mm, 5 mm to 6.5 mm, 5 mm to 6 mm, 5.5 mm to 16 mm, 5.5 mm to 15 mm, 5.5 mm to 14 mm, 5.5 mm to 13 mm, 5.5 mm to 12 mm, 5.5 mm to 10 mm, 5.5 mm to 9 mm, 5.5 mm to 8 mm, 5.5 mm to 7 mm, 5.5 mm to 6.5 mm, 5.5 mm to 6.4 mm, 5.5 mm to 6.3 mm, 5.5 mm to 6.2 mm, 5.5 mm to 6.1 mm, or 5.5 mm to 6 mm. Each possibility represents a separate embodiment of the present invention. The different embodiments can be combined at will.

Optionally, a width 341 measured along the lateral axis of first proximal coupling portion 344 ranges from 0.8 mm to 2 mm, 0.8 mm to 1.8 mm, 0.8 mm to 1.7 mm, 0.8 mm to 1.6 mm, 0.8 mm to 1.5 mm, 0.8 mm to 1.4 mm, 0.8 mm to 1.3 mm, 0.8 mm to 1.2 mm, 0.9 mm to 2 mm, 0.9 mm to 1.8 mm, 0.9 mm to 1.7 mm, 0.9 mm to 1.6 mm, 0.9 mm to 1.5 mm, 0.9 mm to 1.4 mm, 0.8 mm to 1.3 mm, 0.9 mm to 1.2 mm, 1 mm to 2 mm, 1 mm to 1.8 mm, 1 mm to 1.7 mm, 1 mm to 1.6 mm, 1 mm to 1.5 mm, 1 mm to 1 mm, 0.8 mm to 1 mm, 1 mm to 1.2 mm, 1.1 mm to 2 mm, 1.1 mm to 1.8 mm, 1.1 mm to 1.7 mm, 0.8 mm to 1.1 mm, 1.1 mm to 1.5 mm, 1.1 mm to 1.4 mm, 1.1 mm to 1.3 mm, or 1.1 mm to 1.2 mm. Each possibility represents a separate embodiment of the present invention. The different embodiments can be combined at will.

Optionally, width 340 measured within aperture 362 along the lateral axis, exceeds thickness 366 of second planar anchoring element 342 by 0.01 mm to 0.06 mm, 0.01 mm to 0.05 mm, 0.01 mm to 0.04 mm, 0.01 mm to 0.03 mm, 0.01 mm to 0.02 mm, 0.02 mm to 0.06 mm, 0.02 mm to 0.05 mm, 0.02 mm to 0.04 mm, or 0.02 mm to 0.03 mm. Each possibility represents a separate embodiment of the present invention. Optionally, a proximal space 343 measured along the lateral axis between hooks 314a and 314b exceeds thickness 366 of second planar anchoring element 342 by 0.01 mm to 0.06 mm, 0.01 mm to 0.05 mm, 0.01 mm to 0.04 mm, 0.01 mm to 0.03 mm, 0.01 mm to 0.02 mm, 0.02 mm to 0.06 mm, 0.02 mm to 0.05 mm, 0.02 mm to 0.04 mm, or 0.02 mm to 0.03 mm. Each possibility represents a separate embodiment of the present invention. In some embodiments, each of width 340 measured within aperture 362 and space 343 measured along the lateral axis between hooks 314a and 314b independently ranges from 0.34 mm to 0.6 mm, 0.36 mm to 0.6 mm, 0.38 mm to 0.6 mm, 0.4 mm to 0.6 mm, 0.41 mm to 0.6 mm, 0.42 mm to 0.6 mm, 0.43 mm to 0.6 mm, 0.44 mm to 0.6 mm, 0.45 mm to 0.6 mm, 0.46 mm to 0.6 mm, 0.47 mm to 0.6 mm, 0.48 mm to 0.6 mm, 0.49 mm to 0.6 mm, 0.5 mm to 0.6 mm, 0.51 mm to 0.6 mm, 0.52 mm to 0.6 mm, 0.53 mm to 0.58 mm, 0.54 mm to 0.6 mm, 0.55 mm to 0.6 mm, 0.56 mm to 0.6 mm, 0.4 mm to 0.58 mm, 0.41 mm to 0.58 mm, 0.42 mm to 0.58 mm, 0.43 mm to 0.58 mm, 0.44 mm to 0.58 mm, 0.45 mm to 0.58 mm, 0.46 mm to 0.58 mm, 0.47 mm to 0.58 mm, 0.48 mm to 0.58 mm, 0.49 mm to 0.58 mm, 0.5 mm to 0.58 mm, 0.51 mm to 0.58 mm, 0.52 mm to 0.58 mm, 0.53 mm to 0.58 mm, 0.54 mm to 0.58 mm, 0.55 mm to 0.58 mm, 0.56 mm to 0.58 mm, 0.4 mm to 0.56 mm, 0.41 mm to 0.56 mm, 0.42 mm to 0.56 mm, 0.43 mm to 0.56 mm, 0.44 mm to 0.56 mm, 0.45 mm to 0.56 mm, 0.46 mm to 0.56 mm, 0.47 mm to 0.56 mm, 0.48 mm to 0.56 mm, 0.49 mm to 0.56 mm, 0.5 mm to 0.56 mm, 0.51 mm to 0.56 mm, 0.52 mm to 0.56 mm, 0.53 mm to 0.56 mm, 0.54 mm to 0.56 mm, or 0.55 mm to 0.56 mm. Each possibility represents a separate embodiment of the present invention. The different embodiments can be combined at will.

In some embodiments, thickness 364 measured from a posterior to an anterior side of first planar anchoring element 336 and its components (e.g., first proximal coupling portion 344, hooks 314a and 314b) ranges from 0.34 mm to 0.6 mm, 0.36 mm to 0.6 mm, 0.38 mm to 0.6 mm, 0.4 mm to 0.6 mm, 0.41 mm to 0.6 mm, 0.42 mm to 0.6 mm, 0.43 mm to 0.6 mm, 0.44 mm to 0.6 mm, 0.45 mm to 0.6 mm, 0.46 mm to 0.6 mm, 0.47 mm to 0.6 mm, 0.48 mm to 0.6 mm, 0.49 mm to 0.6 mm, 0.5 mm to 0.6 mm, 0.51 mm to 0.6 mm, 0.52 mm to 0.6 mm, 0.53 mm to 0.58 mm, 0.54 mm to 0.6 mm, 0.55 mm to 0.6 mm, 0.56 mm to 0.6 mm, 0.4 mm to 0.58 mm, 0.41 mm to 0.58 mm, 0.42 mm to 0.58 mm, 0.43 mm to 0.58 mm, 0.44 mm to 0.58 mm, 0.45 mm to 0.58 mm, 0.46 mm to 0.58 mm, 0.47 mm to 0.58 mm, 0.48 mm to 0.58 mm, 0.49 mm to 0.58 mm, 0.5 mm to 0.58 mm, 0.51 mm to 0.58 mm, 0.52 mm to 0.58 mm, 0.53 mm to 0.58 mm, 0.54 mm to 0.58 mm, 0.55 mm to 0.58 mm, 0.56 mm to 0.58 mm, 0.4 mm to 0.56 mm, 0.41 mm to 0.56 mm, 0.42 mm to 0.56 mm, 0.43 mm to 0.56 mm, 0.44 mm to 0.56 mm, 0.45 mm to 0.56 mm, 0.46 mm to 0.56 mm, 0.47 mm to 0.56 mm, 0.48 mm to 0.56 mm, 0.49 mm to 0.56 mm, 0.5 mm to 0.56 mm, 0.51 mm to 0.56 mm, 0.52 mm to 0.56 mm, 0.53 mm to 0.56 mm, 0.54 mm to 0.56 mm, or 0.55 mm to 0.56 mm. Each possibility represents a separate embodiment of the present invention. The different embodiments can be combined at will.

Second planar anchoring element 342 may include a second proximal coupling portion 352 and a distal pair of opposing hooks 314c and 314d disposed co-planarly with and extending distally and laterally away from second proximal coupling portion 352.

Optionally, each of hooks 314c and 314d define an inner curvature having a radius R2. In some embodiments radius R2 ranges from 2 mm to 3 mm, 2.1 mm to 3 mm, 2.2 mm to 3 mm, 2.3 mm to 3 mm, 2.4 mm to 3 mm, 2.5 mm to 3 mm, 2 mm to 2.6 mm, 2.1 mm to 2.6 mm, 2.2 mm to 2.6 mm, 2.3 mm to 2.6 mm, 2.4 mm to 2.6 mm, 2 mm to 2.5 mm, 2.1 mm to 2.5 mm, 2.2 mm to 2.5 mm, 2.3 mm to 2.5 mm, 2.4 mm to 2.5 mm, 2 mm to 2.4 mm, 2.1 mm to 2.4 mm, 2.2 mm to 2.4 mm, or 2.3 mm to 2.4 mm. Each possibility represents a separate embodiment of the present invention. The different embodiments can be combined at will.

Optionally, first lateral edge 350c and second lateral edge 350d of hooks 314c and 314d, respectively, may taper along the plane defined by the longitudinal-lateral axes, resulting in a pointed surface on the proximal edge of each of first lateral edge 350c and second lateral edge 350d.

Optionally, second proximal coupling portion 352 includes a pair of spaced apart proximal arms 358 and 360 each comprising a proximal protrusion 358a and 360a, protruding one towards the other. Optionally, a distance 361 between a pair of spaced apart proximal arms 358 and 360 exceeds thickness 364 measured from a posterior to an anterior side of first proximal coupling portion 344 and a proximal distance 365 between proximal protrusions 358a and 360a is less than thickness 364 measured from a posterior to an anterior side of first proximal coupling portion 344. In some embodiments, a distance 361 exceeds thickness 364 in 0.01 mm to 0.06 mm, 0.01 mm to 0.05 mm, 0.01 mm to 0.04 mm, 0.01 mm to 0.03 mm, 0.01 mm to 0.02 mm, 0.02 mm to 0.06 mm, 0.02 mm to 0.05 mm, 0.02 mm to 0.04 mm, or 0.02 mm to 0.03 mm. Each possibility represents a separate embodiment of the present invention. In some embodiments, a proximal distance 363 between proximal protrusions 358a and 360a is less than thickness 364 by a range of 0.01 mm to 0.06 mm, 0.01 mm to 0.05 mm, 0.01 mm to 0.04 mm, 0.01 mm to 0.03 mm, 0.01 mm to 0.02 mm, 0.02 mm to 0.06 mm, 0.02 mm to 0.05 mm, 0.02 mm to 0.04 mm, or 0.02 mm to 0.03 mm. Each possibility represents a separate embodiment of the present invention. The different embodiments can be combined at will.

Optionally, a width 365 measured along the lateral axis of second proximal coupling portion 352 ranges from 0.8 mm to 2 mm, 0.8 mm to 1.8 mm, 0.8 mm to 1.7 mm, 0.8 mm to 1.6 mm, 0.8 mm to 1.5 mm, 0.8 mm to 1.4 mm, 0.8 mm to 1.3 mm, 0.8 mm to 1.2 mm, 0.9 mm to 2 mm, 0.9 mm to 1.8 mm, 0.9 mm to 1.7 mm, 0.9 mm to 1.6 mm, 0.9 mm to 1.5 mm, 0.9 mm to 1.4 mm, 0.8 mm to 1.3 mm, 0.9 mm to 1.2 mm, 1 mm to 2 mm, 1 mm to 1.8 mm, 1 mm to 1.7 mm, 1 mm to 1.6 mm, 1 mm to 1.5 mm, 0.8 mm to 1 mm, 1 mm to 1.2 mm, 1.1 mm to 2 mm, 1.1 mm to 1.8 mm, 1.1 mm to 1.7 mm, 0.8 mm to 1.1 mm, 1.1 mm to 1.5 mm, 1.1 mm to 1.4 mm, 1.1 mm to 1.3 mm, or 1.1 mm to 1.2 mm. Each possibility represents a separate embodiment of the present invention. The different embodiments can be combined at will.

Optionally a In some embodiments, a height 367 measured along the longitudinal axis from proximal end 354 to a distal end of hook 314c or 314d ranges from 4 mm to 16 mm, 4 mm to 15 mm, 4 mm to 14 mm, 4 mm to 13 mm, 4 mm to 12 mm, 4 mm to 10 mm, 4 mm to 9 mm, 4 mm to 8 mm, 4 mm to 7 mm, 4 mm to 6.5 mm, 4 mm to 6 mm, 5 mm to 16 mm, 5 mm to 15 mm, 5 mm to 14 mm, 5 mm to 13 mm, 5 mm to 12 mm, 5 mm to 10 mm, 5 mm to 9 mm, 5 mm to 8 mm, 5 mm to 7 mm, 5 mm to 6.5 mm, 5 mm to 6 mm, 5.5 mm to 16 mm, 5.5 mm to 15 mm, 5.5 mm to 14 mm, 5.5 mm to 13 mm, 5.5 mm to 12 mm, 5.5 mm to 10 mm, 5.5 mm to 9 mm, 5.5 mm to 8 mm, 5.5 mm to 7 mm, 5.5 mm to 6.5 mm, 5.5 mm to 6.4 mm, 5.5 mm to 6.3 mm, 5.5 mm to 6.2 mm, 5.5 mm to 6.1 mm, or 5.5 mm to 6 mm. Each possibility represents a separate embodiment of the present invention. The different embodiments can be combined at will.

In some embodiments, a width 369 measured from first lateral edge 350c to second lateral edge 350d of distal pair of opposing hooks 314c and 314d of second planar anchoring element 342 ranges from 4 mm to 16 mm, 4 mm to 15 mm, 4 mm to 14 mm, 4 mm to 13 mm, 4 mm to 12 mm, 4 mm to 10 mm, 4 mm to 9 mm, 4 mm to 8 mm, 4 mm to 7 mm, 4 mm to 6.5 mm, 4 mm to 6 mm, 8 mm to 12.4 mm, 8 mm to 12.2 mm, 8 mm to 12.1 mm, 8 mm to 12 mm, 8 mm to 11.9 mm, 8 mm to 11.8 mm, 8 mm to 11.7 mm, 8 mm to 11.6 mm, 8 mm to 11.5 mm, 8 mm to 11.4 mm, 8 mm to 11.3 mm, 8 mm to 11.2 mm, 8.5 mm to 13 mm, 8.5 mm to 12.9 mm, 8.5 mm to 12.8 mm, 8.5 mm to 12.7 mm, 8.5 mm to 12.6 mm, 8.5 mm to 12.5 mm, 8.5 mm to 12.4 mm, 8.5 mm to 12.2 mm, 8.5 mm to 12.1 mm, 8.5 mm to 12 mm, 8.5 mm to 11.9 mm, 8.5 mm to 11.8 mm, 8.5 mm to 11.7 mm, 8.5 mm to 11.6 mm, 8.5 mm to 11.5 mm, 8.5 mm to 11.4 mm, 8.5 mm to 11.3 mm, 8.5 mm to 11.2 mm, 9 mm to 13 mm, 9 mm to 12.9 mm, 9 mm to 12.8 mm, 9 mm to 12.7 mm, 9 mm to 12.6 mm, 9 mm to 12.5 mm, 9 mm to 12.4 mm, 9 mm to 12.2 mm, 9 mm to 12.1 mm, 9 mm to 12 mm, 9 mm to 11.9 mm, 9 mm to 11.8 mm, 9 mm to 11.7 mm, 9 mm to 11.6 mm, 9 mm to 11.5 mm, 9 mm to 11.4 mm, 9 mm to 11.3 mm, 9 mm to 11.2 mm, 9.5 mm to 13 mm, 9.5 mm to 12.9 mm, 9.5 mm to 12.8 mm, 9.5 mm to 12.7 mm, 9.5 mm to 12.6 mm, 9.5 mm to 12.5 mm, 9.5 mm to 12.4 mm, 9.5 mm to 12.2 mm, 9.5 mm to 12.1 mm, 9.5 mm to 12 mm, 9.5 mm to 11.9 mm, 9.5 mm to 11.8 mm, 9.5 mm to 11.7 mm, 9.5 mm to 11.6 mm, 9.5 mm to 11.5 mm, 9.5 mm to 11.4 mm, 9.5 mm to 11.3 mm, 9.5 mm to 11.2 mm, 10 mm to 13 mm, 10 mm to 12.9 mm, 10 mm to 12.8 mm, 10 mm to 12.7 mm, 10 mm to 12.6 mm, 10 mm to 12.5 mm, 10 mm to 12.4 mm, 10 mm to 12.2 mm, 10 mm to 12.1 mm, 10 mm to 12 mm, 10 mm to 11.9 mm, 10 mm to 11.8 mm, 10 mm to 11.7 mm, 10 mm to 11.6 mm, 10 mm to 11.5 mm, 10 mm to 11.4 mm, 10 mm to 11.3 mm, 10 mm to 11.2 mm, 10.5 mm to 13 mm, 10.5 mm to 12.9 mm, 10.5 mm to 12.8 mm, 10.5 mm to 12.7 mm, 10.5 mm to 12.6 mm, 10.5 mm to 12.5 mm, 10.5.5 mm to 12.4 mm, 10.5 mm to 12.2 mm, 10.5 mm to 12.1 mm, 10.5 mm to 12 mm, 10.5 mm to 11.9 mm, 10.5 mm to 11.8 mm, 10.5 mm to 11.7 mm, 10.5 mm to 11.6 mm, 10.5 mm to 11.5 mm, 10.5 mm to 11.4 mm, 10.5 mm to 11.3 mm, 10.5 to 11.2 mm, 11 mm to 13 mm, 11 mm to 12.9 mm, 11 mm to 12.8 mm, 11 mm to 12.7 mm, 11 mm to 12.6 mm, 11 mm to 12.5 mm, 11 mm to 12.4 mm, 11 mm to 12.2 mm, 11 mm to 12.1 mm, 11 mm to 12 mm, 11 mm to 11.9 mm, 11 mm to 11.8 mm, 11 mm to 11.7 mm, 11 mm to 11.6 mm, 11 mm to 11.5 mm, 11 mm to 11.4 mm, 11 mm to 11.3 mm, or 11 mm to 11.2 mm. Each possibility represents a separate embodiment of the present invention. The different embodiments can be combined at will.

In some embodiments, a width 368 of hooks 314c and 314d ranges from 0.2 mm to 0.6 mm, 0.2 mm to 0.58 mm, 0.2 mm to 0.56 mm, 0.2 mm to 0.54 mm, 0.2 mm to 0.52 mm 0.2 mm to 0.5 mm, 0.2 mm to 0.48 mm, 0.2 mm to 0.46 mm, 0.2 mm to 0.44 mm, 0.2 mm to 0.42 mm, 0.2 mm to 0.41 mm, 0.2 mm to 0.40 mm, 0.2 mm to 0.39 mm, 0.25 mm to 0.6 mm, 0.25 mm to 0.58 mm, 0.25 mm to 0.56 mm, 0.25 mm to 0.54 mm, 0.25 mm to 0.52 mm 0.25 mm to 0.5 mm, 0.25 mm to 0.48 mm, 0.25 mm to 0.46 mm, 0.25 mm to 0.44 mm, 0.25 mm to 0.42 mm, 0.25 mm to 0.41 mm, 0.25 mm to 0.40 mm, 0.25 mm to 0.39 mm, 0.3 mm to 0.6 mm, 0.3 mm to 0.58 mm, 0.3 mm to 0.56 mm, 0.3 mm to 0.54 mm, 0.3 mm to 0.52 mm 0.3 mm to 0.5 mm, 0.3 mm to 0.48 mm, 0.3 mm to 0.44 mm, 0.3 mm to 0.42 mm, 0.3 mm to 0.41 mm, 0.3 mm to 0.40 mm, 0.3 mm to 0.39 mm, 0.32 mm to 0.6 mm, 0.32 mm to 0.58 mm, 0.32 mm to 0.56 mm, 0.32 mm to 0.54 mm, 0.32 mm to 0.52 mm 0.32 mm to 0.5 mm, 0.32 mm to 0.48 mm, 0.32 mm to 0.44 mm, 0.32 mm to 0.42 mm, 0.32 mm to 0.41 mm, 0.32 mm to 0.40 mm, 0.32 mm to 0.39 mm, 0.34 mm to 0.6 mm, 0.34 mm to 0.58 mm, 0.34 mm to 0.56 mm, 0.34 mm to 0.54 mm, 0.34 mm to 0.52 mm 0.34 mm to 0.5 mm, 0.34 mm to 0.48 mm, 0.34 mm to 0.44 mm, 0.34 mm to 0.42 mm, 0.34 mm to 0.41 mm, 0.34 mm to 0.40 mm, 0.34 mm to 0.39 mm, 0.36 mm to 0.6 mm, 0.36 mm to 0.58 mm, 0.36 mm to 0.56 mm, 0.36 mm to 0.54 mm, 0.36 mm to 0.52 mm 0.36 mm to 0.5 mm, 0.36 mm to 0.48 mm, 0.36 mm to 0.44 mm, 0.36 mm to 0.42 mm, 0.36 mm to 0.41 mm, 0.36 mm to 0.40 mm, 0.36 mm to 0.39 mm, 0.37 mm to 0.6 mm, 0.37 mm to 0.58 mm, 0.37 mm to 0.56 mm, 0.37 mm to 0.54 mm, 0.37 mm to 0.52 mm 0.37 mm to 0.5 mm, 0.37 mm to 0.48 mm, 0.37 mm to 0.44 mm, 0.37 mm to 0.42 mm, 0.37 mm to 0.41 mm, 0.37 mm to 0.40 mm, or 0.37 mm to 0.39 mm. Each possibility represents a separate embodiment of the present invention. The different embodiments can be combined at will.

FIG. 3B(1) shows an alternative to first planar anchoring element 336 of FIG. 3B, with the notable difference being the shape of a proximal end 346a. Whereas proximal end 346 of FIG. 3B has an oblong, arcuate shape, proximal end 346a of FIG. 3B(1) is shaped as an arc with two straight "shoulders". This configuration may be advantageous in preventing clamping or entanglement of the thread connected to the anchoring element, when the anchoring element resides inside the shaft of the present apparatus.

Figure 4:
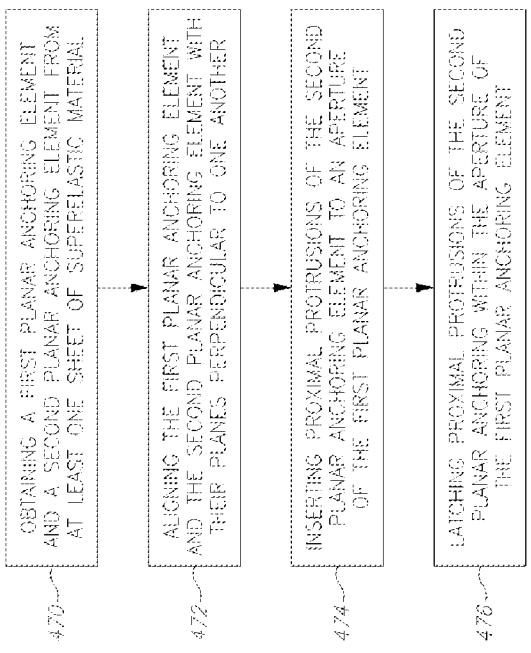
FIG. 4 is a flow chart of the steps of a method for manufacturing the anchor of FIGS. 2A-E, in accordance with an embodiment.

Reference is now made to FIG. 4, which is a flow chart of the method for manufacturing an anchor in accordance with the anchor of FIGS. 3A-E. First planar anchoring element 336 and second planar anchoring element 342 are obtained from at least one sheet of superelastic material (step 470). Optionally, first and second planar anchoring elements 336 and 342 may be obtained by employing a technique selected from the group consisting of: stamping, cutting, molding, and forging. First planar anchoring element 336 and second planar anchoring element 342 are positioned such that their planes define a first angle α and a supplementary angle β between them (step 472). Optionally, first planar anchoring element 336 and second planar anchoring element 342 are positioned with their planes perpendicular to one another. Proximal protrusions 358a and 360a of second planar anchoring element 342 are inserted to aperture 362 of first planar anchoring element 336 (step 474). Optionally, upon insertion, proximal protrusions 358a and 360a, may latch within aperture 362 (step 476).

Figure 5:
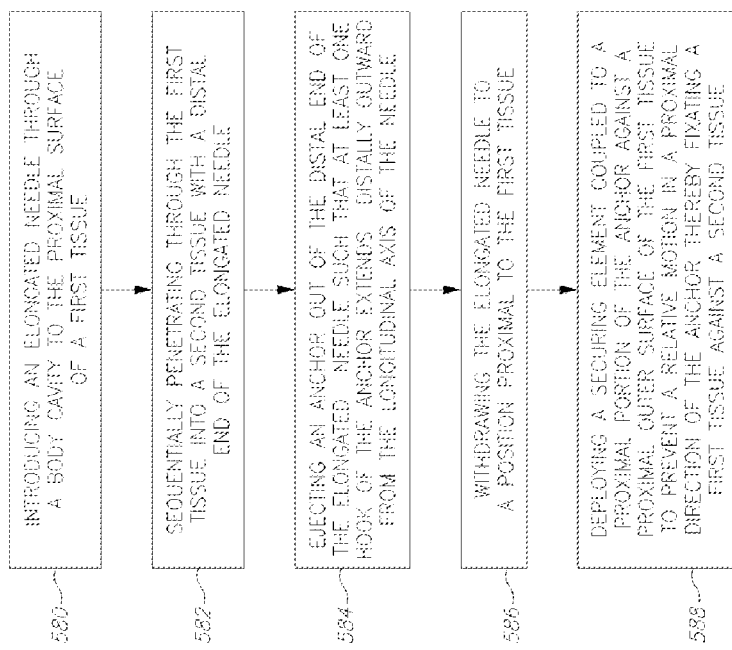
FIG. 5 is a flow chart of the steps of a method for affixing a first tissue to a second tissue, in accordance with an embodiment.

Reference is now made to FIG. 5, which is a flow chart of the method for affixing a first tissue to a second tissue. An elongated needle is introduced through a body cavity to the proximal surface of the first tissue (step 580). In some embodiments, the body cavity is a vaginal cavity. A distal end of the elongated needle is sequentially penetrated through a first and into or beyond a second tissue (step 582). In some embodiments, the first tissue is a vaginal wall and the second tissue is a sacrospinous ligament. An anchor is ejected out of the distal end of the elongated needle such that at least one hook of the anchor extends distally outward from the longitudinal axis of the needle (step 584). Optionally, the at least one hook may extend into or beyond the second tissue. In some embodiments, the at least one hook extends into the second tissue. In some embodiments, the at least one hook extends into a lumen beyond a distal outer surface of the second tissue. The elongated needle is withdrawn to a position proximal to the first tissue (step 586). In some embodiments, in which the anchor is coupled to a thread, the thread is exposed proximal to the first tissue upon withdrawal of the elongated needle. A securing element coupled to a proximal portion of the anchor is deployed against a proximal outer surface of the first tissue to prevent a relative motion in a proximal direction of the anchor thereby affixing a first tissue to a second tissue (step 588). In some embodiments, the securing element is coupled to the proximal portion of the anchor upon deployment. In some embodiments, the securing element is coupled to the proximal portion of the anchor prior to deployment. In some embodiments, the securing element and the anchor are coupled by a thread. In a non-limiting example, in which a thread couples the securing element and the anchor, the thread may be exposed upon withdrawal of the elongated needle in step 584 and upon the deployment of the securing element in step 586, an actuator may be actuated to prevent a sliding of the securing element over the thread in at least one direction.

Optionally, the anchor may be retrieved in a proximal direction by insertion of a wire coupled to the proximal portion of the anchor or by insertion of the proximal end of the anchor into a distal opening of a retrieval device and insertion of the anchor through the distal opening to the retrieval device by pulling the wire in a proximal direction (step 590). Step 590 may be employed prior to step 588. Alternatively, or additionally, step 590 may be employed following detachment of the securing element from the proximal portion of the anchor.

FIGS. 6A-E are schematic illustrations, each illustrating a step of a method for affixing a first tissue (e.g., vaginal wall) to a second tissue (sacrospinous ligament) in accordance with the apparatus of FIGS. 1A-E.

Reference is now made to FIG. 6A which shows a shaft 102 introduced against a proximal surface of a first tissue (e.g., vaginal wall) 690 which is pushed against a second tissue (e.g., sacrospinous ligament) 692.

Reference is now made to FIG. 6B which shows an elongated needle 104 having a distal piercing tip 118 inserted through first tissue (e.g., vaginal wall) 690 into second tissue (e.g., sacrospinous ligament) 692. Optionally, elongated needle may be inserted through first tissue 690 into second tissue 692 by sequentially piercing first tissue 690 and penetrating second tissue 692 with distal piercing tip 118.

Reference is now made to FIG. 6C which shows anchor 108 ejected out of distal opening 116 of elongated needle 102 such that at least one hook 114 extends distally outward from the longitudinal axis of elongated needle 102, into the second tissue (e.g., sacrospinous ligament) 692.

Reference is now made to FIG. 6D which shows anchor 108 proximally coupled to thread 120 which is exposed following withdrawal of elongated needle 104 and shaft 102 to a position proximal to first tissue 690 (not shown).

Reference is now made to FIG. 6E which shows securing element 106 deployed against the proximal portion of the vaginal wall 690, thereby affixing first tissue (e.g., vaginal wall) 690 to second tissue (e.g., sacrospinous ligament) 692. Optionally, an actuator (not shown) is actuated, to prevent the sliding of securing element 106 over thread 120 in at least one direction.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicated number and a second indicated number and "ranging/ranges from" a first indicated number "to" a second indicated number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements. Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur in a different order than the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or act or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for sacrospinous ligament fixation, the method comprising the steps of:
   (a) providing a kit comprising (i) an apparatus comprising: (A) an elongated needle, (B) a superelastic anchor disposed within said elongated needle, (C) a securing element, and (D) a user-triggerable advancement mechanism, and (ii) a retrieval device comprising a distal tube section having an inner diameter smaller than an uncompressed uncontracted diameter of the anchor such that a proximal withdrawal of the anchor into the distal tube section is effective to radially contract the anchor to a contracted state;
   (b) vaginally introducing said elongated needle and sequentially piercing a vaginal wall and penetrating a sacrospinous ligament with a distal end of said elongated needle;
   (b) ejecting the superelastic anchor out of the distal end of said elongated needle from within said elongated needle such that said superelastic anchor extends distally outward from the longitudinal axis of the needle, into the sacrospinous ligament;
   (c) withdrawing said elongated needle to a position proximal to the vaginal wall; and
   (d) ejecting said securing element from the apparatus against a proximal portion of the vaginal wall, to prevent a movement of the anchor in at least one direction,
   thereby affixing the vaginal wall against the sacrospinous ligament.

2. The method of claim 1, wherein said anchor comprises:
   (a) a first planar anchoring element obtained from a sheet of a superelastic material, and comprising:
      a first proximal coupling portion having an aperture extending between a posterior side and an anterior side of said proximal coupling portion, and
      a distal pair of opposing hooks disposed co-planarly with said first proximal coupling portion and extending distally and laterally away in from said first proximal coupling portion; and
   (b) a second planar anchoring element obtained from a sheet of a superelastic material, and comprising:
      a second proximal coupling portion comprising:
         a pair of spaced apart proximal arms each comprising a proximal protrusion, wherein said proximal protrusions of said arms protrude one towards the other, wherein a proximal distance between said proximal protrusions is less than a thickness measured from a posterior to an anterior side of said first coupling element, and
      a distal pair of opposing hooks disposed co-planarly with said second proximal coupling portion and extending distally and laterally away from said second proximal coupling portion,
   wherein said first and said second planar anchoring elements are coupled together by a latching of said proximal protrusions of said second planar anchoring element to said aperture of said first planar anchoring element.

3. The method of claim 1, further comprising retrieving the anchor from within the sacrospinous ligament by:
   threading a wire that is connected to the anchor, through the distal tube section of the retrieval device;
   pushing a distal end of the distal tube section of the retrieval device into the sacrospinous ligament, such that a proximal portion of the anchor is inserted into the tube;
   pulling the wire proximally, such that the anchor is withdrawn proximally into the distal tube section and is radially contracted to a contracted state within the retrieval device; and
   withdrawing the distal tube section, the anchor disposed therewithin, from the sacrospinous ligament.

4. The method of claim 3, wherein the proximal portion of the anchor comprises the first and second proximal coupling portions of the anchor.

5. A kit comprising:
(a) an apparatus comprising: (i) an elongated needle, (ii) a superelastic anchor disposed within said elongated needle, (iii) a securing element, and (iv) a user-triggerable advancement mechanism, the apparatus being configured when triggered to eject said anchor out of a distal end of said elongated needle to allow said superelastic anchor to extend distally outward from the elongated needle through a vaginal wall and into a sacrospinous ligament, and following the ejection of said anchor, eject said securing element from the apparatus to prevent movement of said anchor in at least one direction; and
(b) a retrieval device comprising a distal tube section having an inner diameter smaller than an uncompressed uncontracted diameter of the anchor, such that a proximal withdrawal of the anchor into the distal tube section is effective to radially contract the anchor to a contracted state.

6. The kit of claim 5, wherein the distal tube section of said retrieval device is configured to thread through said distal tube section a retrieving wire connected to the anchor, such that (i) a distal advancement of the distal tube section surrounding said retrieving wire is effective to bring a distal tip of said distal tube section to a proximal portion of the anchor and (ii) a proximal withdrawal of said retrieving wire is effective to cause the anchor to retract into said distal tube section and contract to fit within said distal tube section.

7. The kit of claim 6, wherein said distal tube section is flexible.

8. The kit of claim 6, wherein the retrieval device comprises a flexible joint proximal to said distal tube section and distal to a proximal tube section.

9. The kit of claim 8, wherein a flexibility of said flexible joint is such that bringing said distal tip to said proximal portion of the anchor includes said distal tip self-guiding to encircle a base of the anchor.

10. The kit of claim 8, wherein in said distal advancement of the distal tube section surrounding said retrieving wire, the distal tube section is effective to flex, at said flexible joint, in any radial dimension until said distal tip encircles the base of the anchor.

* * * * *